(12) United States Patent
Kortagere et al.

(10) Patent No.: US 11,345,696 B2
(45) Date of Patent: May 31, 2022

(54) COMPOUNDS AND METHODS OF TREATING OR AMELIORATING AN IL-1R-MEDIATED DISEASE OR DISORDER USING SAME

(71) Applicant: DREXEL UNIVERSITY, Philadelphia, PA (US)

(72) Inventors: Sandhya Kortagere, Newtown, PA (US); Carol M. Artlett, Chesterbrook, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 16/537,897

(22) Filed: Aug. 12, 2019

(65) Prior Publication Data

US 2019/0367503 A1 Dec. 5, 2019

Related U.S. Application Data

(63) Continuation of application No. 15/726,911, filed on Oct. 6, 2017, now Pat. No. 10,428,059, which is a continuation of application No. 15/328,281, filed as application No. PCT/US2015/043403 on Aug. 3, 2015, now abandoned.

(60) Provisional application No. 62/032,668, filed on Aug. 4, 2014.

(51) Int. Cl.
| | |
|---|---|
| A61K 31/4162 | (2006.01) |
| C07D 417/14 | (2006.01) |
| C07D 401/04 | (2006.01) |
| A61K 45/06 | (2006.01) |
| A61K 31/47 | (2006.01) |
| A61K 31/519 | (2006.01) |
| C07C 317/44 | (2006.01) |
| C07D 211/90 | (2006.01) |
| C07D 215/54 | (2006.01) |
| C07D 249/08 | (2006.01) |
| C07D 309/32 | (2006.01) |
| C07D 317/58 | (2006.01) |
| C07D 317/66 | (2006.01) |
| C07D 471/04 | (2006.01) |
| C07D 487/04 | (2006.01) |
| C07D 491/052 | (2006.01) |
| C07D 493/04 | (2006.01) |
| C07D 513/04 | (2006.01) |
| A61K 31/167 | (2006.01) |
| A61K 31/36 | (2006.01) |
| A61K 31/427 | (2006.01) |
| A61K 31/4439 | (2006.01) |
| C07C 237/52 | (2006.01) |
| C07D 263/56 | (2006.01) |
| A61K 38/00 | (2006.01) |

(52) U.S. Cl.
CPC .......... *C07D 417/14* (2013.01); *A61K 31/167* (2013.01); *A61K 31/36* (2013.01); *A61K 31/4162* (2013.01); *A61K 31/427* (2013.01); *A61K 31/4439* (2013.01); *A61K 31/47* (2013.01); *A61K 31/519* (2013.01); *A61K 45/06* (2013.01); *C07C 237/52* (2013.01); *C07C 317/44* (2013.01); *C07D 211/90* (2013.01); *C07D 215/54* (2013.01); *C07D 249/08* (2013.01); *C07D 263/56* (2013.01); *C07D 309/32* (2013.01); *C07D 317/58* (2013.01); *C07D 317/66* (2013.01); *C07D 401/04* (2013.01); *C07D 471/04* (2013.01); *C07D 487/04* (2013.01); *C07D 491/052* (2013.01); *C07D 493/04* (2013.01); *C07D 513/04* (2013.01); *A61K 38/00* (2013.01); *C07C 2601/08* (2017.05); *C07C 2601/14* (2017.05)

(58) Field of Classification Search
CPC .................................................. A61K 31/4162
See application file for complete search history.

(56) References Cited

U.S. PATENT DOCUMENTS

| | | | |
|---|---|---|---|
| 6,911,211 B2 | 6/2005 | Eini et al. | |
| 8,183,386 B2* | 5/2012 | Hirao ..................... | H05K 3/282 |
| | | | 548/343.5 |
| 2006/0094663 A1 | 5/2006 | Chemtob et al. | |
| 2008/0311209 A1 | 12/2008 | Beumer et al. | |
| 2010/0035867 A1 | 2/2010 | Guerrant et al. | |
| 2011/0053975 A1 | 3/2011 | Tazi et al. | |
| 2011/0112140 A1 | 5/2011 | Miyata et al. | |
| 2014/0142146 A1 | 5/2014 | Lemieux et al. | |

FOREIGN PATENT DOCUMENTS

| | | |
|---|---|---|
| KR | 10-0808551 | 3/2008 |
| WO | 9629088 A1 | 9/1996 |
| WO | 0149287 A1 | 7/2001 |

(Continued)

OTHER PUBLICATIONS

PubChem CID 2839556, National Center for Biotechnology Information. PubChem Compound Summary for CID 2839556. https://pubchem.ncbi.nlm.nih.gov/compound/2839556. Accessed Oct. 22, 2021, create date Jul. 28, 2005. (Year: 2005).*

PubChem CID 600800, National Center for Biotechnology Information. PubChem Compound Summary for CID 600800. https://pubchem.ncbi.nlm.nih.gov/compound/600800. Accessed Oct. 22, 2021, create date Mar. 27, 2005. (Year: 2005).*

(Continued)

*Primary Examiner* — Laura L Stockton
(74) *Attorney, Agent, or Firm* — Saul Ewing Arnstein & Lehr LLP; Kathryn Doyle; Domingos J. Silva

(57) ABSTRACT

The present invention provides compounds useful for treating or preventing an IL-1R-mediated disease or disorder. In certain embodiments, the disease or disorder comprises scleroderma.

10 Claims, 10 Drawing Sheets

(56) References Cited

FOREIGN PATENT DOCUMENTS

| WO | 03072528 A2 | 9/2003 |
|---|---|---|
| WO | 2006003517 A1 | 1/2006 |
| WO | 2006075808 A1 | 7/2006 |
| WO | 2007051062 A2 | 5/2007 |
| WO | 2008097640 A2 | 8/2008 |
| WO | 2008103470 A2 | 8/2008 |
| WO | 2009100035 A2 | 8/2009 |
| WO | 2009123241 A1 | 10/2009 |
| WO | 2012080729 A2 | 6/2012 |
| WO | 2012154403 A2 | 11/2012 |
| WO | 2013183016 A1 | 12/2013 |
| WO | 2015153959 A2 | 10/2015 |
| WO | 2016037255 A2 | 3/2016 |

OTHER PUBLICATIONS

PubChem CID 46183364 {National Center for Biotechnology Information. PubChem Compound Summary for CID 46183364. https://pubchem.ncbi.nlm.nih.gov/compound/methyl-3-naphthalen-1-yl-1H-indole-2-carboxylate. Accessed Oct. 22, 2021, create date Jul. 6, 2010. (Year: 2010).*

Chemical Abstracts Registry No. 4073-72-7. indexed in the Registry file on STN Case Online on Nov. 16, 1984.

Chemical Abstracts Registry No. 876722-14-4, indexed in the Registry file on STN CAS Online on Mar. 14, 2006.

International Search Report and Written Opinion for PCT International Application No. PCT/US2015/043403 dated Nov. 2, 2015.

Partial Supplementary European Search Report dated Feb. 21, 2018 for European Patent Application No. 15829982.6.

PubChem BioAssay AID 1022, National Center for Biotechnology Information. PubChem BioAssay Database MD=1022, https://pubchem.ncbi.nlm.nih.gov/ bioassay/1022 (accessed Sep. 5, 2018), deposit date Jan. 8, 2008. (Year: 2008).

PubChem BioAssay AI D 1417, National Center for Biotechnology Information. PubChem BioAssay Database; AI D=1417, https://pubchem .ncbi .nlm .nih .gov/bioassay/1417 (accessed Sep. 5, 2018), deposit date Oct. 29, 2008. (Year: 2008).

PubChem CID 2930969—National Center for Biotechnology Information. PubChem Compound Database CID=2930969, <https://pubchem.ncbi.nlm.nih.gov/compound/2930969 (accessed Jun. 29, 2017), create date Jul. 29, 2005.

PubChem CID 4887504, National Center for Biotechnology Information. PubChem Compound Database CID=4887504, https://pubchem.ncbi.nlm.nih.gov/compound/4887504 (accessed Sep. 5, 2018), create date Sep. 17, 2005. (Year: 2005).

CAS Registry No. 570392-85-7, Aug. 2003.
CAS Registry No. 570392-88-0, Aug. 2003.
CAS Registry No. 311763-04-9, Dec. 2000.
CAS Registry No. 375838-28-1, Dec. 2001.
CAS Registry No. 299449-69-7, Dec. 2004.
CAS Registry No. 299452-80-5, Dec. 2004.
CAS Registry No. 301321-31-3, Dec. 2004.
CAS Registry No. 330848-50-5, Dec. 2004.
CAS Registry No. 333309-04-9, Dec. 2004.
CAS Registry No. 801226-85-7, Dec. 2004.
CAS Registry No. 957356-09-1, Dec. 2007.
CAS Registry No. 957500-20-8, Dec. 2007.
CAS Registry No. 957506-43-3, Dec. 2007.
CAS Registry No. 823193-98-2, Jan. 2005.
CAS Registry No. 552304-29-7, Jul. 2003.
CAS Registry No. 557068-15-2, Jul. 2003.
CAS Registry No. 854067-45-1, Jul. 2005.
CAS Registry No. 857669-83-1, Jul. 2005.
CAS Registry No. 846561-10-2, Jul. 2007.
CAS Registry No. 878684-37-8, Jul. 2007.
CAS Registry No. 943062-73-5, Jul. 2007.
CAS Registry No. 853113-30-1, Jun. 2005.
CAS Registry No. 326020-60-4, Mar. 2001.
CAS Registry No. 845287-42-5, Mar. 2005.
CAS Registry No. 498536-83-7, Mar. 2006.
CAS Registry No. 876722-14-4, Mar. 2006.
CAS Registry No. 876886-26-9, Mar. 2006.
CAS Registry No. 1298268-79-7, May 2011.
CAS Registry No. 332910-19-7, Oct. 2002.
CAS Registry No. 460318-51-8, Oct. 2002.
CAS Registry No. 756829-71-7, Oct. 2004.
CAS Registry No. 581078-84-4, Sep. 2003.

Al-Masoudi, et al., "Synthesis and anti-HIV Activity of New Fused Chromene Derivatives Derived from 2-Amino-4-(1-naphthyl)-5-oxo-4H,5H-pyrano[3,2-c]chromene-3-carbonitrile", Z. Naturforsch. 68(3), 2013, 229-238.

Doan, et al., "Rheumatoid arthritis: an overview of new and emerging therapies", J Clin Pharmacol. 45(7), Jul. 2005, 751-762.

Dotsenko, et al., "Design and synthesis of pyrido[2,1-b][1,3,5]thiadiazine library via uncatalyzed Mannich-type reaction", ACS Comb Sci. 16(10), 2014, S1-S83.

Dotsenko, et al., "Design and synthesis of pyrido[2,1-b][1,3,5]thiadiazine library via uncatalyzed Mannich-type reactionACS Comb Sci. Oct. 13, 2014;16(10):543-50", ACS Comb Sci. 16(10), 2014, 543-550.

Evdokimov, et al., "Structural simplification of bioactive natural products with multicomponent synthesis. 3. Fused uracil-containing heterocycles as novel topoisomerase-targeting agents", J Med Chem. 54(7), Apr. 2011, 2012-2021.

Kots, et al., "Pyridopyrimidine derivatives as inhibitors of cyclic nucleotide synthesis: Application for treatment of diarrhea". Proc Natl Acad Sci USA. 105(24), Jun. 2008, 8440-8445.

Tu, et al., "A Simple Synthesis of Furo[3',4':5,6]pyrido[2,3-d]pyrimidine Derivatives through Multicomponent Reactions in Water", Eur. J. Org. Chem. 9, 2007, 1522-1528.

* cited by examiner

FIG. 3
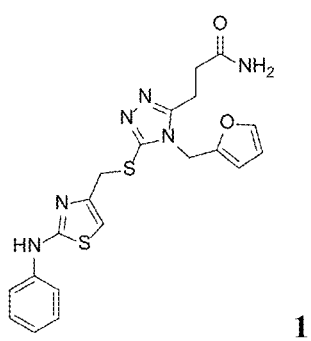
1
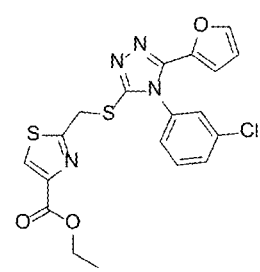
2
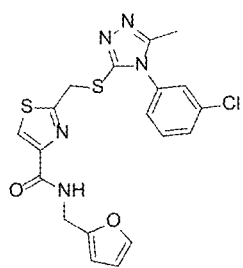
3
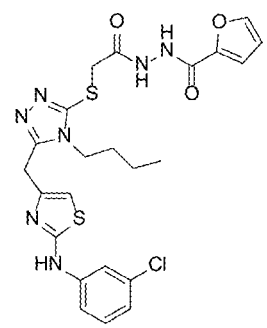
4
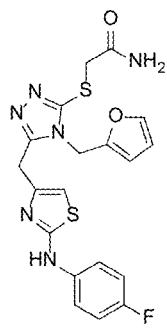
5
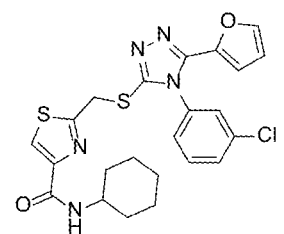
6

FIG. 4

| compound | structure |
|---|---|
| KA862<br><br>(Cyclohexyl {[5-({2-[(3-chlorophenyl)amino]-1,3-thiazol-4-yl}methyl)-4-(2-furylmethyl)-4H-1,2,4-triazol-3-yl]sulfanyl} acetate) | 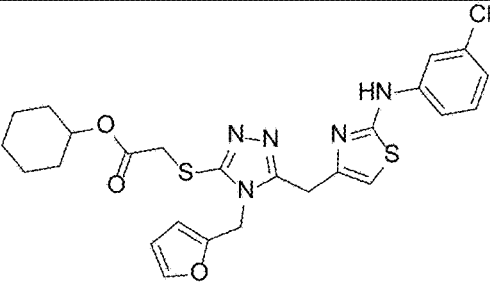 |
| KA494<br><br>(N-Cyclohexyl-$N^2$-[({2-[(4-fluorophenyl)amino]-2-oxoethyl} sulfinyl)acetyl]-$N^2$-1-naphthylglycinamide) | 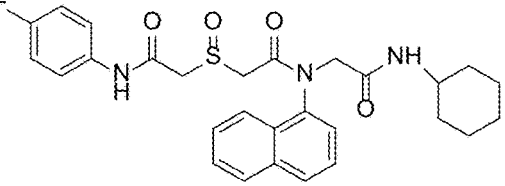 |
| KA529<br><br>(2-[5-{[2-(Cyclopentylamino)-2-oxoethyl]sulfanyl}-3-(4-pyridinyl)-1H-1,2,4-triazol-1-yl]-N-(3-methoxyphenyl)acetamide) | 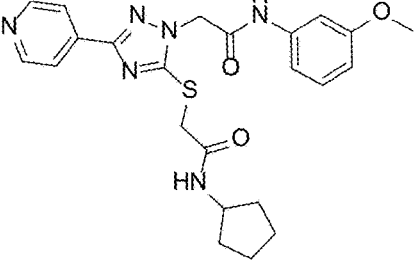 |
| KA199<br><br>($N^2$-(1,3-Benzodioxol-5-ylmethyl)-$N^2$-{[4-(cyclopentylsulfamoyl) phenyl]sulfonyl}-N-phenylglycinamide) | 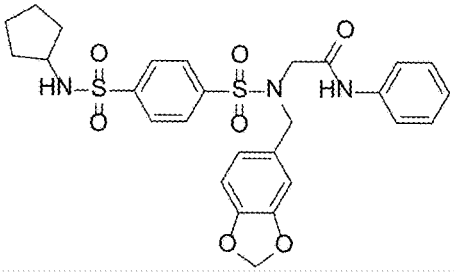 |
| KA680<br><br>($N^2$-({[2-(1,3-Benzodioxol-5-ylamino)-2-oxoethyl]sulfinyl} acetyl)-$N^2$-(2-chlorobenzyl)-N-cyclopentylglycinamide) | 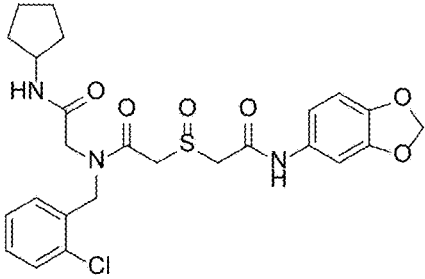 |

FIG. 5
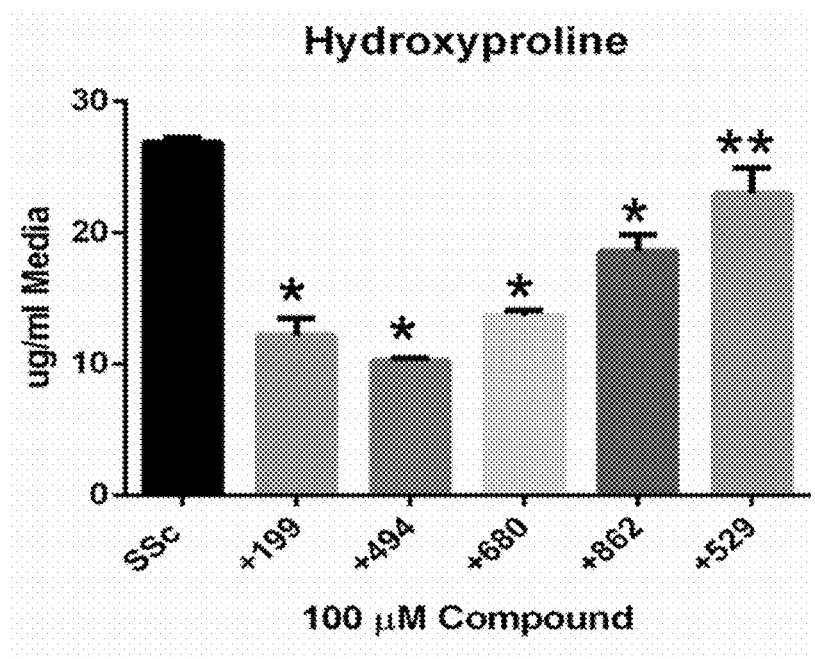
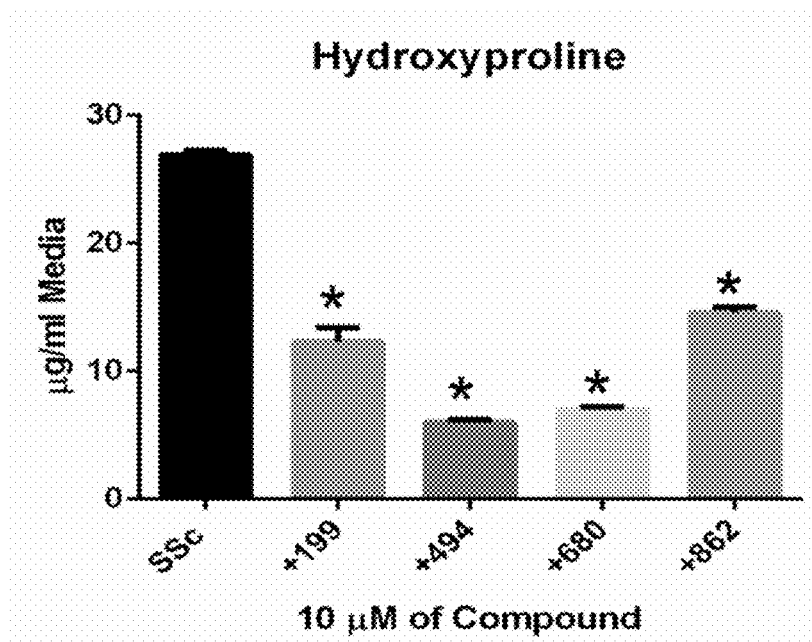

COMPOUNDS AND METHODS OF TREATING OR AMELIORATING AN IL-1R-MEDIATED DISEASE OR DISORDER USING SAME

CROSS-REFERENCE TO RELATED APPLICATIONS

The present application is a continuation of, and claims priority to, U.S. patent application Ser. No. 15/726,911, filed Oct. 6, 2017, now allowed, which is a continuation of, and claims priority to, U.S. patent application Ser. No. 15/328,281, filed Jan. 23, 2017, now abandoned, which is a 35 U.S.C. § 371 national phase application from, and claims priority to, International Application No. PCT/US2015/043403, filed Aug. 3, 2015 and published under PCT Article 21(2) in English, which claims priority under 35 U.S.C. § 119(e) to U.S. Provisional Patent Application No. 62/032,668, filed Aug. 4, 2014.

BACKGROUND OF THE INVENTION

Scleroderma, also known as systemic sclerosis, is a chronic systemic autoimmune disease that primarily affects the skin and is characterized by hardening (sclerosis) of the skin and internal organs due to the excessive accumulation of collagen. Further, scleroderma is characterized by damage to small blood vessels, activation of T lymphocytes and production of antinuclear antibodies.

Limited scleroderma involves cutaneous manifestations that mainly affect the hands, arms and face, with the following common manifestations: calcinosis (deposition of calcium nodules in the skin), Raynaud's phenomenon (exaggerated vasoconstriction in the hands, with fingers undergoing white-blue-red color transitions in the cold), esophageal dysfunction (leading to difficulty swallowing), sclerodactyly (skin thickening on the fingers), and telangiectasias (dilated capillaries on the face, hands and mucous membranes) with internal organ involvement many years after disease diagnosis. On the other hand, diffuse scleroderma progresses rapidly and is quite disabling, affecting a large area of the skin and internal organs, such as the kidneys, esophagus, heart and/or lungs.

The prognosis is dire for limited cutaneous scleroderma patients who escape pulmonary complications (they generally die of lung failure within 30 years post diagnosis), but is even 35742656.1 worse for those with the diffuse cutaneous disease, particularly in patients who are older and/or male. Death occurs most often from pulmonary, heart and kidney complications. In diffuse cutaneous disease, five-year survival is about 70% and 10-year survival is about 55%.

Scleroderma is of unknown etiology, but is often thought to be an autoimmune condition. Further, strong associations between scleroderma and certain mutations in the human leukocyte antigen (HLA) gene and/or environmental factors have been identified.

There are no approved treatments or cures for scleroderma itself, but individual organ system complications may be treated. Systemic disease-modifying treatment with immunosuppressants is often used in scleroderma. Immunosuppressants used include azathioprine, methotrexate, cyclophosphamide, mycophenolate mofetil, intravenous immunoglobulin, rituximab, sirolimus, alefacept, and the tyrosine kinase inhibitors, imatinib, nilotinib and dasatinib. Experimental therapies currently under investigation include endothelin receptor antagonists, tyrosine kinase inhibitors, beta-glycan peptides, halofuginone, basiliximab, alemtuzumab, abatacept and hematopoietic stem cell transplantation.

Anakinra (KINERET®) and rilonacept (ARCALYST®) are currently undergoing clinical trials for the treatment of scleroderma. These drugs, which are large recombinant proteins requiring direct infusions, directly target interleukin 1 (IL-1) signaling by either interfering with the IL-1 receptor (IL-1R) or sequestering IL-1 from the circulation. Anakinra is a human IL-1R antagonist, binding to IL-1R and blocking its binding of IL-1α or IL-1β. Rilonacept is a dimeric protein comprising the ligand-binding domains of the extracellular portions of the human IL-1R and human IL-1R accessory protein linked to the Fc portion of human immunoglobulin G1 (IgG1). Rilonacept binds and neutralizes circulating IL-1. Anakinra and rilonacept are also used in treating other autoimmune diseases such as rheumatoid arthritis, lupus, and Sjogren's syndrome.

Currently there is a critical lack of approved therapies for IL-1R-mediated diseases or disorders, such as the orphan disease scleroderma. There is thus a need in the art for novel therapeutic compounds that treat or ameliorate scleroderma, or a complication or symptom thereof, in mammals. The present invention fulfills this need.

BRIEF SUMMARY OF THE INVENTION

The invention provides compound, or a salt, tautomer or solvate thereof. The invention further provides pharmaceutical compounds comprising at least one compound of the invention.

The invention further provides a method of treating or ameliorating an IL-1R-mediated disease or disorder in a mammal in need thereof, the method comprising administering to the mammal a therapeutically effective amount of at least one compound of the invention, whereby the disease or disorder is treated or ameliorated.

In certain embodiments, the compound of the invention is selected from the group consisting of:
(i) a compound of formula (I):

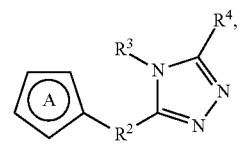

wherein in (I),
ring A is selected from the group consisting of:

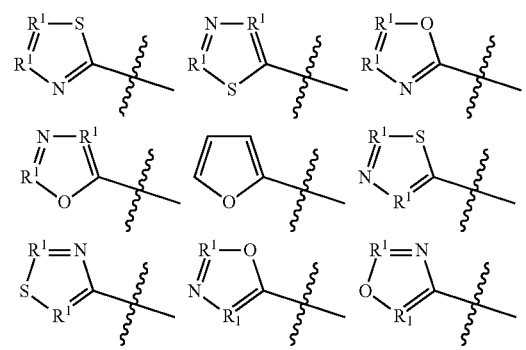

-continued

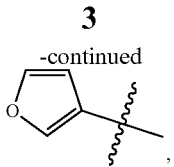

wherein in ring A one occurrence of $R^1$ is $CR^6$ and the other occurrence of $R^1$ is N or $CR^7$ and the furan rings are independently optionally substituted with $R^7$;

$R^2$ is selected from the group consisting of bond, —$CH_2S$—, —$SCH_2$—, —$CH_2O$—, —$OCH_2$—, —$(CH_2)_{1-6}$—, arylene, heteroarylene, and combinations thereof;

$R^3$ is selected from the group consisting of —$C_1$-$C_6$ alkyl, —$C_2$-$C_6$ alkenyl, —$C_1$-$C_6$ heteroalkyl, —($C_0$-$C_3$ alkyl)-($C_3$-$C_8$ cycloalkyl), —($C_0$-$C_3$ alkyl)-($C_4$-$C_{10}$ heterocyclyl), —($C_0$-$C_3$ alkyl)-($C_6$-$C_{10}$ aryl) and —($C_0$-$C_3$ alkyl)-($C_5$-$C_{10}$ heteroaryl), wherein the alkyl, alkenyl, heteroalkyl, cycloalkyl, heterocyclyl, aryl or heteroaryl group is independently optionally substituted;

$R^4$ is selected from the group consisting of —$C_1$-$C_6$ alkyl, —$C_1$-$C_6$ heteroalkyl, —($C_0$-$C_3$ alkyl)-($C_3$-$C_8$ cycloalkyl), —($C_0$-$C_3$ alkyl)-($C_4$-$C_{10}$ heterocyclyl), —($C_0$-$C_3$ alkyl)-($C_6$-$C_{10}$ aryl), —($C_0$-$C_3$ alkyl)-($C_5$-$C_{10}$ heteroaryl), —$(CH_2)_{1-3}$—$C(=O)NH_2$, —$(CH_2)_{1-3}$—$C(=O)NHNHC(=O)R^5$, —$S(CH_2)_{1-3}$—$C(=O)NH_2$, —$S(CH_2)_{1-3}$—$C(=O)NHR^8$, —$S(CH_2)_{1-3}$—$C(=O)OR^3$ and —$S(CH_2)_{1-3}$—$C(=O)NHNHC(=O)R^5$, wherein the alkyl, heteroalkyl, heterocyclyl, aryl or heteroaryl group is independently optionally substituted;

each occurrence of $R^5$ is independently —$C_4$-$C_{10}$ heterocyclyl, —$C_6$-$C_{10}$ aryl or —$C_5$-$C_{10}$ heteroaryl, wherein the heterocyclyl, aryl or heteroaryl group is independently optionally substituted;

each occurrence of $R^6$ is independently selected from the group consisting of —$NHR^8$, —$C(=O)OH$, —$C(=O)OR^8$ and —$C(=O)NHR^8$;

each occurrence of $R^1$ is independently H, halo, —$C_1$-$C_6$ alkyl or —$C_3$-$C_{10}$ cycloalkyl, wherein the alkyl or cycloalkyl group is independently optionally substituted; and, each occurrence of $R^8$ is independently selected from the group consisting of —$C_1$-$C_6$ alkyl, —$C_1$-$C_6$ heteroalkyl, —($C_0$-$C_3$ alkyl)-($C_3$-$C_8$ cycloalkyl), —($C_0$-$C_3$ alkyl)-($C_4$-$C_{10}$ heterocyclyl), —($C_0$-$C_3$ alkyl)-($C_6$-$C_{10}$ aryl) and —($C_0$-$C_3$ alkyl)-($C_5$-$C_{10}$ heteroaryl), wherein the alkyl, heteroalkyl, cycloalkyl, heterocyclyl, aryl or heteroaryl group is independently optionally substituted;

(ii) a compound of formula (II):

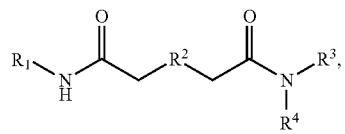

wherein in (II):

$R^1$ and $R^3$ are independently selected from the group consisting of —($C_0$-$C_3$ alkyl)-($C_6$-$C_{10}$ aryl), and —($C_0$-$C_3$ alkyl)-($C_5$-$C_{10}$ heteroaryl), wherein the alkyl, aryl or heteroaryl group is independently optionally substituted;

$R^2$ is S, S(=O) or S(=O)$_2$;

$R^4$ is selected from the group consisting of —$(CH_2)_{1-3}$$C(=O)OH$, —$(CH_2)_{1-3}$$C(=O)OR^5$ and —$(CH_2)_{1-3}$$C(=O)NHR^5$; and, each occurrence of $R^5$ is independently selected from the group consisting of —$C_1$-$C_6$ alkyl, —$C_1$-$C_6$ heteroalkyl, —($C_0$-$C_3$ alkyl)-($C_3$-$C_8$ cycloalkyl), —($C_0$-$C_3$ alkyl)-($C_4$-$C_{10}$ heterocyclyl), —($C_0$-$C_3$ alkyl)-($C_6$-$C_{10}$ aryl) and —($C_0$-$C_3$ alkyl)-($C_5$-$C_{10}$ heteroaryl), wherein the alkyl, heteroalkyl, cycloalkyl, heterocyclyl, aryl or heteroaryl group is independently optionally substituted;

(iii) a compound of formula (III):

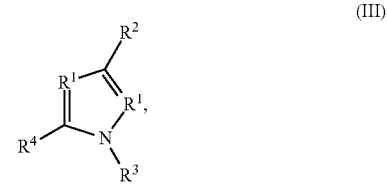

wherein in (III), each occurrence of $R^1$ is independently N or $CR^6$;

$R^2$ is selected from the group consisting of —($C_0$-$C_3$ alkyl)-($C_4$-$C_{10}$ heterocyclyl), —($C_0$-$C_3$ alkyl)-($C_6$-$C_{10}$ aryl) and —($C_0$-$C_3$ alkyl)-($C_5$-$C_{10}$ heteroaryl), wherein the alkyl, heterocyclyl, aryl or heteroaryl group is independently optionally substituted;

$R^3$ and $R^4$ are independently selected from the group consisting of —$(CH_2)_{1-3}$—$C(=O)OR^5$, —$(CH_2)_{1-3}$—$C(=O)NH_2$, —$(CH_2)_{1-3}$—$C(=O)NHR^5$, —$S(CH_2)_{1-3}$—$C(=O)NH_2$, —$S(CH_2)_{1-3}$—$C(=O)OR^5$ and —$S(CH_2)_{1-3}$—$C(=O)NHR^5$;

each occurrence of $R^5$ is independently H, —$C_1$-$C_6$ alkyl, —$C_3$-$C_{10}$ cycloalkyl, —$C_6$-$C_{10}$ aryl, or heteroaryl, wherein the alkyl, cycloalkyl, aryl or heteroaryl group is independently optionally substituted; and, each occurrence of $R^6$ is independently H, halo, —$C_1$-$C_6$ alkyl, —$C_3$-$C_{10}$ cycloalkyl, —$C_6$-$C_{10}$ aryl, or heteroaryl, wherein the alkyl, cycloalkyl, aryl or heteroaryl group is independently optionally substituted;

(iv) a compound of formula (IV):

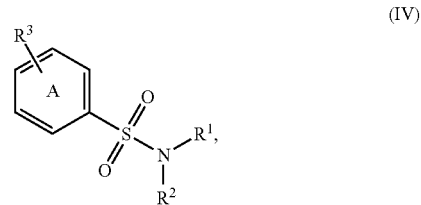

wherein in (IV), $R^1$ is selected from the group consisting of —($C_0$-$C_3$ alkyl)-($C_4$-$C_{10}$ heterocyclyl), —($C_0$-$C_3$ alkyl)-($C_6$-$C_{10}$ aryl) and —($C_0$-$C_3$ alkyl)-($C_5$-$C_{10}$ heteroaryl), wherein the alkyl, heterocyclyl, aryl or heteroaryl group is independently optionally substituted;

$R^2$ is selected from the group consisting of —$(CH_2)_{1-3}$—$C(=O)OR^4$, —$(CH_2)_{1-3}$—$C(=O)NH_2$, and —$(CH_2)_{1-3}$—$C(=O)NHR^4$;

$R^3$ is —$C(=O)OR^4$, —$C(=O)NHR^4$ or —$S(=O)_2NHR^4$;

each occurrence of $R^4$ is independently H, —$C_1$-$C_6$ alkyl, —$C_3$-$C_{10}$ cycloalkyl, —$C_6$-$C_{10}$ aryl, or heteroaryl, wherein the alkyl, cycloalkyl, aryl or heteroaryl group is independently optionally substituted; and, A ring is optionally further substituted;

(v) a compound of formula (V):

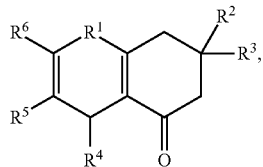

(V)

wherein in (V),

R¹ is selected from the group consisting of O, NH and N(C₁-C₆ alkyl), wherein the alkyl group is optionally substituted;

R² is selected from the group consisting of H and —(C₁-C₆ alkyl), wherein the alkyl group is optionally substituted;

R³ is selected from the group consisting of H, —(C₁-C₆ alkyl) and aryl, wherein the alkyl or aryl group is optionally substituted;

R⁴ is optionally substituted aryl;

R⁵ is selected from the group consisting of —CN, —C(=O)OH and —C(=O)O(C₁-C₆ alkyl), wherein the alkyl group is optionally substituted; and R⁶ is methyl or NH₂;

(vi) the compound of formula (VI), 3-(furan-2-ylmethyl)-8-(naphthalen-1-yl)-6-oxo-3,4,7,8-tetrahydro-2H,6H-pyrido[2,1-b][1,3,5]thiadiazine-9-carbonitrile:

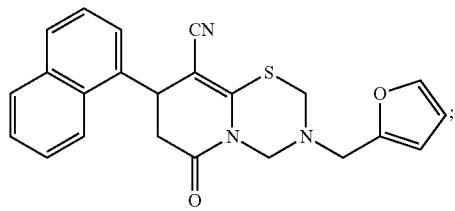

(VI)

(vii) the compound of formula (VII), 6-amino-4-(2-hydroxynaphthalen-1-yl)-3-methyl-1-phenyl-1,4-dihydropyrano[2,3-c]pyrazole-5-carbonitrile:

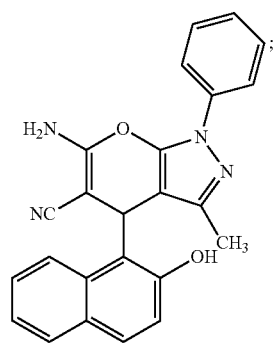

(VII)

(viii) the compound of formula (VIII), 2-((3-cyano-4-(naphthalen-1-yl)-6-oxo-1,4,5,6-tetrahydropyridin-2-yl)thio)-N-phenylacetamide:

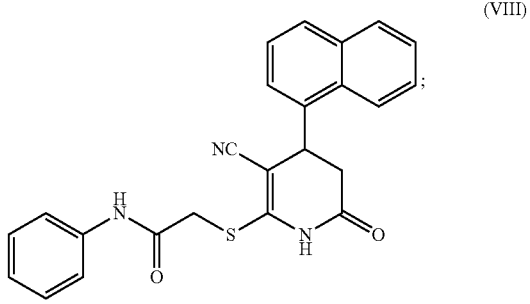 [SMILES: N#CC1=C(SCC(=O)Nc2ccccc2)NC(=O)CC1c1cccc2ccccc12]

(VIII)

(ix) the compound of formula (IX), methyl 6-amino-5-cyano-2-(methoxymethyl)-4-(naphthalen-1-yl)-4H-pyran-3-carboxylate:

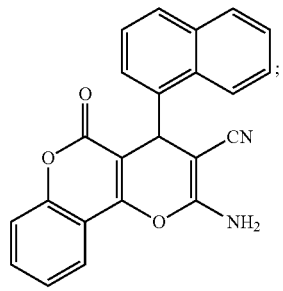

(IX)

(x) the compound of formula (X), 2-amino-4-(naphthalen-1-yl)-5-oxo-4H,5H-pyrano[3,2-c]chromene-3-carbonitrile:

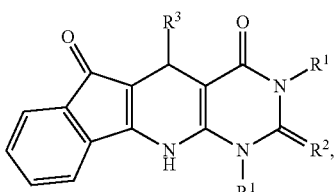

(X)

(xi) a compound of formula (XI):

(XI)

wherein in (XI):

each occurrence of R¹ is independently selected from the group consisting of H and methyl;

R² is O or —NH; and

R³ is optionally substituted phenyl or naphthyl;

(xii) a compound of formula (XII):

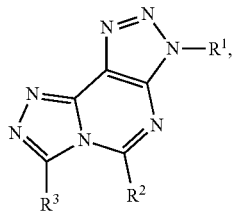

(XII)

wherein in (XII):
R¹ is phenyl or benzyl, wherein the phenyl or benzyl group is optionally substituted;
R² is H or methyl; and,
R³ is optionally substituted phenyl;
(xiii) a compound of formula (XIII):

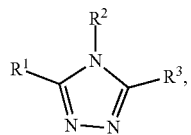

(XIII)

wherein in (XIII):
R¹ is optionally substituted phenyl;
R² is optionally substituted phenyl; and,
R³ is optionally substituted phenyl or heteroaryl;
and any mixtures thereof.

In certain embodiments, in (I) ring A is selected from the group consisting of:

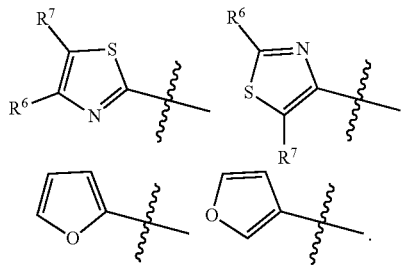

In other embodiments, in (I) in ring A one occurrence of $R^1$ is $CR^6$ and the other occurrence of $R^1$ is $CR^7$. In yet other embodiments, in (I) $R^2$ is selected from the group consisting of —$CH_2S$—, —$SCH_2$— and —$(CH_2)_{1-6}$—. In yet other embodiments, in (I) $R^3$ is selected from the group consisting of —$C_1$-$C_6$ alkyl, —$C_2$-$C_6$ alkenyl, —$C_3$-$C_8$ cycloalkyl, —$(C_0$-$C_3$ alkyl)-$(C_6$-$C_{10}$ aryl) and —$(C_0$-$C_3$ alkyl)-$(C_5$-$C_{10}$ heteroaryl), wherein the alkyl, alkenyl cycloalkyl, aryl or heteroaryl group is independently optionally substituted. In yet other embodiments, in (I) $R^4$ is selected from the group consisting of $C_1$-$C_6$ alkyl, —$(C_0$-$C_3$ alkyl)-$(C_6$-$C_{10}$ aryl), —$(C_0$-$C_3$ alkyl)-$(C_5$-$C_{10}$ heteroaryl), —$(CH_2)_{1-3}$—$C(=O)$ $NH_2$, —$S(CH_2)_{1-3}$—$C(=O)NH_2$, —$S(CH_2)_{1-3}$—$C(=O)$ $OR^3$ and —$S(CH_2)_{1-3}$—$C(=O)NHNHC(=O)R^5$. In yet other embodiments, in (I) $R^5$ is $C_6$-$C_{10}$ aryl or $C_5$-$C_{10}$ heteroaryl, wherein the aryl or heteroaryl group is independently optionally substituted. In yet other embodiments, in (I) $R^6$ is selected from the group consisting of —$NHR^8$ and —$C(=O)NHR^8$. In yet other embodiments, in (I) $R^7$ is H, halo or $C_1$-$C_6$ alkyl, wherein the alkyl group is optionally substituted. In yet other embodiments, in (I) $R^8$ is selected from the group consisting of —$(C_0$-$C_3$ alkyl)-$(C_3$-$C_8$ cycloalkyl), —$(C_0$-$C_3$ alkyl)-$(C_6$-$C_{10}$ aryl) and —$(C_0$-$C_3$ alkyl)-$(C_5$-$C_{10}$ heteroaryl), wherein the alkyl, heteroalkyl, cycloalkyl, aryl or heteroaryl group is independently optionally substituted.

In certain embodiments, in (II) $R^1$ and $R^3$ are independently selected from the group consisting of —$(C_6$-$C_{10}$ aryl) and —$(C_5$-$C_{10}$ heteroaryl), wherein the aryl or heteroaryl group is independently optionally substituted. In other embodiments, in (II) $R^2$ is —$S(=O)$— or —$S(=O)_2$—. In yet other embodiments, in (II) $R^4$ is —$(CH_2)_{1-3}C(=O)$ $NHR^5$. In yet other embodiments, in (II) $R^5$ is selected from the group consisting of —$C_1$-$C_6$ alkyl, —$(C_0$-$C_3$ alkyl)-$(C_3$-$C_8$ cycloalkyl), —$(C_0$-$C_3$ alkyl)-$(C_4$-$C_{10}$ heterocyclyl), —$(C_0$-$C_3$ alkyl)-$(C_6$-$C_{10}$ aryl), and —$(C_0$-$C_3$ alkyl)-$(C_5$-$C_{10}$ heteroaryl), wherein the alkyl, cycloalkyl, heterocyclyl, aryl or heteroaryl group is independently optionally substituted.

In certain embodiments, in (III) each occurrence of $R^1$ is N. In other embodiments, in (III) $R^3$ is selected from the group consisting of —$S(CH_2)_{1-3}$—$C(=O)NH_2$, —$S(CH_2)_{1-3}$—$C(=O)OR^5$ and —$S(CH_2)_{1-3}$—$C(=O)$ $NHR^5$. In yet other embodiments, in (III) $R^4$ is selected from the group consisting of —$(CH_2)_{1-3}$—$C(=O)OR^5$, —$(CH_2)_{1-3}$—$C(=O)NH_2$, and —$(CH_2)_{1-3}$—$C(=O)NHR^5$.

In certain embodiments, in (IV) $R^1$ is selected from the group consisting of —$CH_2$—$(C_4$-$C_{10}$ heterocyclyl), —$CH_2$—$(C_6$-$C_{10}$ aryl) and —$CH_2$—$(C_5$-$C_{10}$ heteroaryl). In other embodiments, in (IV) $R^2$ is —$(CH_2)_{1-3}$—$C(=O)$ $NHR^4$. In yet other embodiments, in (IV) $R^3$ is —$S(=O)_2$ $NHR^4$.

In certain embodiments, the compound of the invention is at least one selected from the group consisting of: cyclohexyl 2-((5-((2-((3-chlorophenyl)amino)thiazol-4-yl)methyl)-4-(furan-2-yl methyl)-4H-1,2,4-triazol-3-yl)thio)acetate; 3-(4-(furan-2-ylmethyl)-5-(((2-(phenylamino)thiazol-4-yl)methyl)thio)-4H-1,2,4-triazol-3-yl)propanamide; ethyl 2-(((4-(3-chlorophenyl)-5-(furan-2-yl)-4H-1,2,4-triazol-3-yl)thio)methyl) thiazole-4-carboxylate; 2-(((4-(3-chlorophenyl)-5-methyl-4H-1,2,4-triazol-3-yl)thio)methyl)-N-(furan-2-yl methyl)thiazole-4-carboxamide; N'-(2-((4-butyl-5-((2-((3-chlorophenyl)amino)thiazol-4-yl)methyl)-4H-1,2,4-triazol-3-yl)thio)acetyl)furan-2-carbohydrazide; 2-((5-((2-((4-fluorophenyl)amino)thiazol-4-yl)methyl)-4-(furan-2-ylmethyl)-4H-1,2,4-triazol-3-yl)thio)acetamide; 2-(((4-(3-chlorophenyl)-5-(furan-2-yl)-4H-1,2,4-triazol-3-yl)thio) methyl)-N-cyclohexylthiazole-4-carboxamide; 2-((4-allyl-5-(furan-2-yl)-4H-1,2,4-triazol-3-yl)thio)-N-(benzo[d] thiazol-2-yl) acetamide; N-(4,5-dimethylthiazol-2-yl)-2-((4-ethyl-5-(furan-2-yl)-4H-1,2,4-triazol-3-yl)thio)acetamide; 2-((5-((2-((4-ethoxyphenyl)amino)thiazol-4-yl)methyl)-4-ethyl-4H-1,2,4-triazol-3-yl)thio)-N-(furan-2-ylmethyl)acetamide; N-(2-(cyclohexyl amino)-2-oxoethyl)-2-((2-((4-fluorophenyl)amino)-2-oxoethyl) sulfinyl)-N-(naphthalen-1-yl) acetamide; (N-cyclohexyl-N2-[({2-[(4-fluorophenyl)amino]-2-oxoethyl}sulfinyl)acetyl]-N²-1-naphthylglycinamide); (N²-({[2-(1,3-benzodioxol-5-yl amino)-2-oxoethyl] sulfinyl}acetyl)-N²-(2-chlorobenzyl)-N-cyclopentylglycinamide); N-(2-(tert-butylamino)-2-oxoethyl)-2-((2-((4-fluorophenyl)amino)-2-oxoethyl) sulfinyl)-N-(m-tolyl)acetamide; (2-[5-{[2-(cyclopentylamino)-2-oxoethyl]sulfanyl}-3-(4-pyridinyl)-1H-1,2,4-triazol-1-yl]-N-(3-methoxy phenyl)acetamide); N²-(1,3-benzodioxol-5-ylmethyl)-N²-{[4-(cyclopentylsulfamoyl)phenyl]sulfonyl}-N-phenylglycinamide; 2-amino-4-(2,7-diethoxynaphthalen-1-yl)-7,7-dimethyl-5-oxo-5,6,7,8-tetrahydro-4H-chromene-3-carbonitrile; ethyl 2-methyl-4-(naphthalen-1-yl)-5-oxo-7-phenyl-1,4,5,6,7,8-hexahydroquinoline-3-carboxylate; methyl 7-(3,4-dimethoxyphenyl)-2-methyl-4-(naphthalen-1-yl)-5-oxo-1,4,5,6,7,8-hexahydroquinoline-3-carboxylate; 2-methoxyethyl 2-methyl-4-(naphthalen-1-yl)-5-oxo-1,4,5,6,7,8-hexahydroquinoline-3-carboxylate; methyl 7-(4-methoxyphenyl)-2-methyl-4-(naphthalen-1-yl)-5-oxo-1,4,5,6,7,8-hexahydroquinoline-3-carboxylate; ethyl 4-(anthracen-9-yl)-2,7,7-trimethyl-5-oxo-1,4,5,6,7,8-hexahydroquinoline-3-carboxylate (KA820); 3-(furan-2-ylmethyl)-8-(naphthalen-1-yl)-6-oxo-3,4,7,8-tetrahydro-2H,6H-pyrido[2,1-b][1,3,5]thiadiazine-9-carbonitrile; 6-amino-4-(2-hydroxynaphthalen-1-yl)-3-methyl-1-phenyl-1,4-dihydropyrano[2,3-c]pyrazole-5-carbonitrile; 2-((3-cyano-4-(naphthalen-1-yl)-6-oxo-1,4,5,6-tetrahydropyridin-2-yl)thio)-N-phenylacetamide; methyl 6-amino-5-cyano-2-(methoxymethyl)-4-(naphthalen-1-yl)-4H-pyran-3-carboxylate; 2-amino-4-(naphthalen-1-yl)-5-oxo-4H,5H-pyrano[3,2-c]chromene-3-carbonitrile; 1,3-dimethyl-5-(naphthalen-1-yl)-5,11-dihydro-1H-indeno[2',1':5,6]pyrido[2,3-d]pyrimidine-2,4,6(3H)-trione; 2-amino-5-(naphthalen-1-yl)-5,11-dihydro-1H-indeno[2',1':5,6]pyrido[2,3-d]pyrimidine-4,6-dione; 3-(4-chlorophenyl)-7-(4-fluorophenyl)-3H-[1,2,3]triazolo[4,5-e][1,2,4]triazolo[4,3-c]pyrimidine; 3-(2-chlorobenzyl)-7-(4-fluorophenyl)-5-methyl-3H-[1,2,3]triazolo[4,5-e][1,2,4]triazolo[4,3-c]pyrimidine; 7-(4-(1H-tetrazol-1-yl)phenyl)-3-(2-chlorobenzyl)-3H-[1,2,3]triazolo[4,5-e][1,2,4]triazolo[4,3-c]pyrimidine; 4-(5-(4-butoxyphenyl)-4-phenyl-4H-1,2,4-triazol-3-yl)-2-(p-tolyl)quinolone; 4-(5-(4-(tert-butyl)phenyl)-4-(p-tolyl)-4H-1,2,4-triazol-3-yl)pyridine; 3-(5-(4-butoxyphenyl)-4-phenyl-4H-1,2,4-triazol-3-yl)aniline; or a salt, tautomer or solvate thereof.

In certain embodiments, the pharmaceutical composition further comprises a pharmaceutically acceptable carrier. In other embodiments, the compound is formulated as a pharmaceutical composition. In other embodiments, the pharmaceutical composition further comprises at least one additional therapeutic agent selected from the group consisting of anakinra, rilonacept, azathioprine, methotrexate, bosentan, etanercept, halofuginone, iloprost, cyclophosphamide, cyclosporin A, mycophenolate mofetil, intravenous immunoglobulin, pirfenidone, prednisone, rituximab, beta-glycan peptides, basiliximab, sirolimus, alefacept, terguride, pomalidomide, and a tyrosine kinase inhibitor.

In certain embodiments, the disease or disorder is an infectious, inflammatory or autoimmune disease or disorder. In other embodiments, the disease or disorder is selected from the group consisting of scleroderma, inflammation in general, systemic lupus erythematosus (lupus), Sjogren's syndrome, arthritis, myositis, Behcet's disease, inflammatory bowel disease, colitis, septic shock, chronic myelogenous leukemia, acute myelogenous leukemia, multiple myeloma, non-blood cancers, psoriasis, type I and type II diabetes, asbestosis, idiopathic pulmonary fibrosis, graft-versus-host disease, familial Mediterranean fever, stroke, epilepsy, and cryopyrin-associated periodic syndromes (CAPS). In yet other embodiments, the non-blood cancer comprises at least one selected from the group consisting of glioma, metastatic breast cancer, interleukin-1-producing cancer, pancreatic ductal adenocarcinoma, colorectal, melanoma, gastric carcinoma, cervical cancer, lung carcinoma, and ovarian carcinoma.

In certain embodiments, the mammal is further administered at least one additional therapeutic agent. In other embodiments, the additional therapeutic agent comprises at least one selected from the group consisting of anakinra, rilonacept, azathioprine, methotrexate, bosentan, etanercept, halofuginone, iloprost, cyclophosphamide, cyclosporin A, mycophenolate mofetil, intravenous immunoglobulin, pirfenidone, prednisone, rituximab, beta-glycan peptides, basiliximab, sirolimus, alefacept, terguride, pomalidomide, and a tyrosine kinase inhibitor. In yet other embodiments, the mammal and the additional therapeutic agent are co-administered to the mammal. In yet other embodiments, the compound is administered to the mammal a given period of time before or after the additional therapeutic agent is administered to the mammal. In yet other embodiments, the mammal is human.

BRIEF DESCRIPTION OF THE DRAWINGS

The following detailed description of specific embodiments of the invention will be better understood when read in conjunction with the appended drawings. For the purpose of illustrating the invention, there are shown in the drawings specific embodiments. It should be understood, however, that the invention is not limited to the precise arrangements and instrumentalities of the embodiments shown in the drawings.

FIG. 3 is a non-limiting illustration of representative compounds of the invention.

FIG. 4 is a non-limiting illustration of representative compounds of the invention.

FIG. 5 is a set of graphs illustrating target validation studies. Selected small molecules downregulated collagen synthesis in SSc fibroblasts. SSc dermal fibroblasts were treated for 48 h with 100 µM or 10 µM of compound, then media was collected and total collagen was measured by hydroxyproline. Samples were tested in triplicate across different patient samples and expressed as the mean±SEM (n=4). *$p<0.0001$, **$p=0.02$.

DETAILED DESCRIPTION OF THE INVENTION

Figure 1:
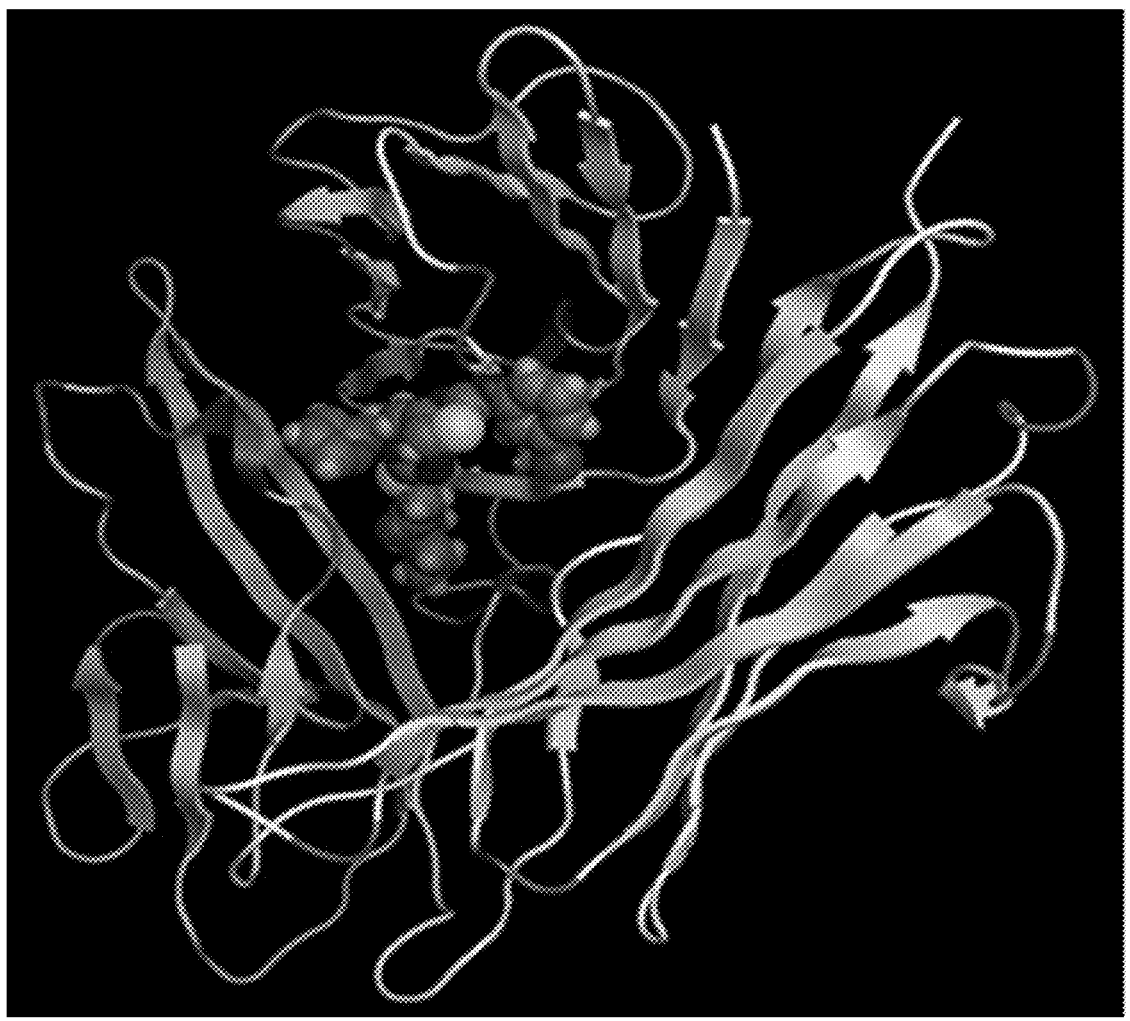
FIG. 1 is a non-limiting schematic representation of the in silico modeling of a compound of the invention bound to IL-1R. IL-1R is represented as ribbons
Figure 2:
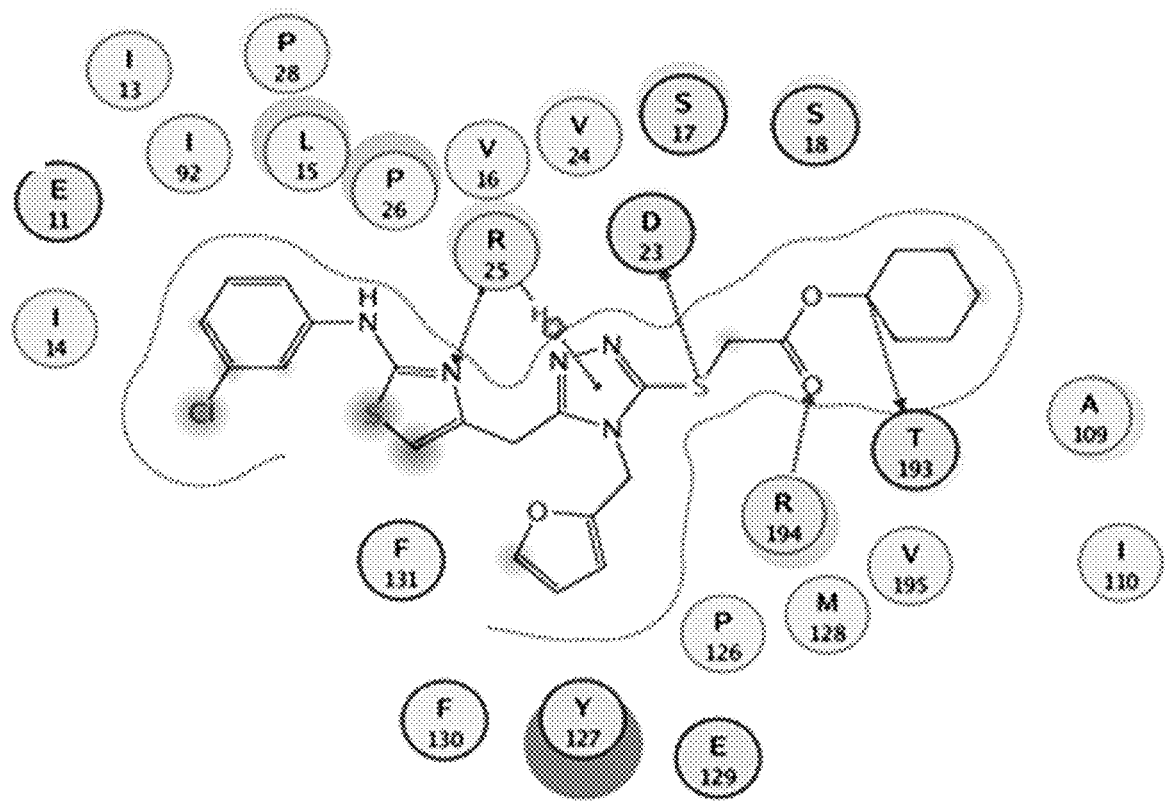
FIG. 2 is a non-limiting schematic representation of KA862 bound to IL-1R.

The present invention relates to the unexpected discovery of small molecule compounds that are useful to treat or ameliorate an IL-1R-mediated disease or disorder in a mammal. In certain embodiments, the disease or disorder includes scleroderma. In other embodiments, the compounds of the invention inhibit or modulate IL-1R signaling. In other embodiments, the compounds of the invention block or modulate the synthesis of collagen in the mammal and thus block or modulate fibrosis in the mammal. In yet other embodiments, the compounds of the invention are useful in combination with other therapeutic agents, such as but not limited to anakinra and/or rilonacept.

In one aspect, the compounds of the invention are useful in treating any IL-1R-mediated diseases or disorders. In certain embodiments, the compounds of the invention are useful in treating or preventing infectious, inflammatory and/or autoimmune diseases or disorders, not limited to scleroderma, and inflammation in general, such as systemic lupus erythematosus (lupus), Sjogren's syndrome, arthritis [including rheumatoid arthritis, juvenile rheumatoid arthritis (also known as juvenile idiopathic arthritis or Still's disease), adult onset Still's disease, psoriatic arthritis, osteoarthritis, and spondylarthritis], myositis [including polymyositis, dermatomyositis, inclusion body myositis], Behcet's disease, inflammatory bowel disease, colitis, septic shock, chronic myelogenous leukemia, acute myelogenous leukemia, multiple myeloma, non-blood cancers (such as, but not limited to, glioma, metastatic breast cancer, cancers producing interleukin-1, pancreatic ductal adenocarcinoma, colorectal, melanoma, gastric carcinoma, cervical cancer, lung carcinoma, and ovarian carcinoma), psoriasis, type I and type II diabetes, asbestosis, idiopathic pulmonary fibrosis, graft-versus-host disease, familial Mediterranean fever, stroke, epilepsy, and cryopyrin-associated periodic syndromes (CAPS, including familial cold autoinflammatory syndrome, Muckle-Wells syndrome and neonatal onset multisystem inflammatory disease).

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "about" as used herein, when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are $C_1$-$C_3$ alkoxy, particularly ethoxy and methoxy.

As used herein, the term "alkyl" by itself or as part of another substituent means, unless otherwise stated, a straight or branched chain hydrocarbon having the number of carbon atoms designated (i.e., $C_{1-6}$ means one to six carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Examples include $C_1$-$C_6$ alkyl, particularly ethyl, methyl, isopropyl, isobutyl, n-pentyl, n-hexyl and cyclopropylmethyl. $C_0$ alkyl corresponds to a bond.

As used herein, the term "substituted alkyl" means alkyl, as defined above, substituted by one, two or three substituents selected from the group consisting of halogen, —OH, alkoxy, —$NH_2$, —$N(CH_3)_2$, —C(=O)OH, trifluoromethyl, —C(=O)O($C_1$-$C_4$)alkyl, —C(=O)$NH_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O)OH, more preferably selected from halogen, alkoxy and —OH. Examples of substituted alkyls include, but are not limited to, 2,2-difluoropropyl, 2-carboxy cyclopentyl and 3-chloropropyl.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-($C_1$-$C_3$ alkyl)" means a functional group wherein a one to three carbon alkylene chain is attached to an aryl group, e.g., —$CH_2CH_2$-phenyl. Preferred is aryl-$CH_2$— and aryl-CH($CH_3$)—. The term "substituted aryl-($C_1$-$C_3$ alkyl)" means an aryl-($C_1$-$C_3$ alkyl) functional group in which the aryl group is substituted. Preferred is substituted aryl($CH_2$)—. Similarly, the term "heteroaryl-($C_1$-$C_3$ alkyl)" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$)alkyl" means a heteroaryl-($C_1$-$C_3$ alkyl) functional group in which the heteroaryl group is substituted. Preferred is substituted heteroaryl-($CH_2$)—.

The term "container" includes any receptacle for holding the pharmaceutical composition. For example, in certain embodiments, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing an IL-1R-mediated disease or disorder in a patient.

As used herein, the terms "effective amount" and "pharmaceutically effective amount" and "therapeutically effective amount" refer to a nontoxic but sufficient amount of an agent or compound to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S (=O)—$CH_3$. Up to two heteroatoms may be consecutive, such as, for example, —$CH_2$—NH—$OCH_3$, or —$CH_2$—$CH_2$—S—S—$CH_3$ As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "IL-1R-mediated disease or disorder" refers to any disease or disorder that is triggered, caused, potentiated, exacerbated, intensified, complicated and/or compounded by the normal or abnormally increased concentration, expression level and/or activity of IL-1R in a mammal. The normal or abnormally increased concentration, expression level and/or activity of IL-1R in a mammal may be determined by examining a mammal who is healthy and/not affected by such disease or disorder. Non-limiting examples of IL-1R-mediated diseases or disorders are infectious, inflammatory and/or autoimmune diseases or disorders, not limited to scleroderma, inflammation in general, systemic lupus erythematosus (lupus), Sjogren's syndrome, arthritis [including rheumatoid arthritis, juvenile rheumatoid arthritis (also known as juvenile idiopathic arthritis or Still's disease), adult onset Still's disease, psoriatic arthritis, osteoarthritis, and spondylarthritis], myositis [including polymyositis, dermatomyositis, inclusion body myositis], Behcet's disease, inflammatory bowel disease, colitis, septic shock, chronic myelogenous leukemia, acute myelogenous leukemia, multiple myeloma, non-blood cancers (such as, but not limited to, glioma, metastatic breast cancer, cancers producing interleukin-1, pancreatic ductal adenocarcinoma, colorectal, melanoma, gastric carcinoma, cervical cancer, lung carcinoma, and ovarian carcinoma), psoriasis, type I and type II diabetes, asbestosis, idiopathic pulmonary fibrosis, graft-versus-host disease, familial Mediterranean fever, stroke, epilepsy, and cryopyrin-associated periodic syndromes (CAPS, including familial cold autoinflammatory syndrome, Muckle-Wells syndrome and neonatal onset multisystem inflammatory disease).

As used herein, the term "KA199" refers to the compound ($N^2$-(1,3-Benzodioxol-5-ylmethyl)-$N^2$-{[4-(cyclopentylsulfamoyl)phenyl]sulfonyl}-N-phenylglycinamide), or a salt, tautomer or solvate thereof.

As used herein, the term "KA222" refers to the compound 6-amino-4-(2-hydroxynaphthalen-1-yl)-3-methyl-1-phenyl-1,4-dihydropyrano[2,3-c]pyrazole-5-carbonitrile, or a salt, tautomer or solvate thereof.

As used herein, the term "KA306" refers to the compound methyl 7-(3,4-dimethoxyphenyl)-2-methyl-4-(naphthalen-1-yl)-5-oxo-1,4,5,6,7,8-hexahydroquinoline-3-carboxylate, or a salt, tautomer or solvate thereof.

As used herein, the term "KA494" refers to the compound N-(2-(cyclohexylamino)-2-oxoethyl)-2-((2-(4-fluorophenyl)amino)-2-oxoethyl)sulfinyl)-N-(naphthalen-1-yl)acetamide, or a salt, tautomer or solvate thereof.

As used herein, the term "KA521" refers to the compound 7-(4-(1H-tetrazol-1-yl)phenyl)-3-(2-chlorobenzyl)-3H-[1,2,3]triazolo[4,5-e][1,2,4]triazolo[4,3-c]pyrimidine, or a salt, tautomer or solvate thereof.

As used herein, the term "KA529" refers to the compound 2-[5-{[2-(cyclopentylamino)-2-oxoethyl]sulfanyl}-3-(4-pyridinyl)-1H-1,2,4-triazol-1-yl]-N-(3-methoxyphenyl)acetamide, or a salt, tautomer or solvate thereof.

As used herein, the term "KA680" refers to $N^2$-({[2-(1,3-benzodioxol-5-ylamino)-2-oxoethyl]sulfinyl}acetyl)-$N^2$-(2-chlorobenzyl)-N-cyclopentylglycinamide, or a salt, tautomer or solvate thereof.

As used herein, the term "KA695" refers to the compound 2-methoxyethyl 2-methyl-4-(naphthalen-1-yl)-5-oxo-1,4,5,6,7,8-hexahydroquinoline-3-carboxylate, or a salt, tautomer or solvate thereof.

As used herein, the term "KA862" refers to the compound cyclohexyl 2-((5-((2-((3-chlorophenyl)amino)thiazol-4-yl)methyl)-4-(furan-2-ylmethyl)-4H-1,2,4-triazol-3-yl)thio)acetate, or a salt, tautomer or solvate thereof.

As used herein, the terms "patient" and "subject" and "individual" refer interchangeably to a human or a non-human mammal. Non-human mammals include, for example, livestock and pets, such as ovine, bovine, porcine, canine, feline and murine mammals. Preferably, the patient or subject is human.

As used herein, the term "pharmaceutical composition" refers to a mixture of at least one compound useful in the methods of the invention with a pharmaceutically acceptable carrier. The pharmaceutical composition facilitates administration of the compound to a patient. Multiple techniques of administering a compound exist in the art including, but not limited to, intravenous, oral, aerosol, parenteral, ophthalmic, pulmonary and topical administration.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful in the methods of the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful in the methods of the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful in the methods of the invention, and are physiologically acceptable to the patient. Supplementary active compounds may also be incorporated into the compositions. The "pharmaceutically acceptable carrier" may further include a pharmaceutically acceptable salt of the compound useful in the methods of the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "salts" embraces addition salts of free acids or bases that are useful within the methods of the invention. In certain embodiments, the salts are pharmaceutically acceptable salts. The language "pharmaceutically acceptable salt" refers to a salt of the administered compounds prepared from pharmaceutically acceptable non-toxic acids or bases, including inorganic acids or bases, organic acids or bases, and solvates, hydrates, or clathrates thereof. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxy benzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluene sulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the invention include, for example, ammonium salts, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, the term "substituted" means that an atom or group of atoms has replaced hydrogen as the substituent attached to another group.

For aryl, aryl-($C_1$-$C_3$ alkyl) and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet other embodiments, the substituents vary in number between one and two. In yet other embodiments, the substituents are independently selected from the group consisting of $C_1$-$C_6$ alkyl, —OH, $C_1$-$C_6$ alkoxy, halo, amino, acetamido and nitro. In yet other embodiments, the substituents are independently selected from the group consisting of $C_1$-$C_6$ alkyl, $C_1$-$C_6$ alkoxy, halo, acetamido, and nitro. As used herein, where a substituent is an alkyl or alkoxy group, the carbon chain may be branched, straight or cyclic, with straight being preferred.

As used herein, the term "treatment" or "treating," is defined as the application or administration of a therapeutic compound, i.e., a compound of the invention (alone or in combination with another therapeutic agent), to a patient, or application or administration of a therapeutic compound to an isolated tissue or cell line from a patient (e.g., for diagnosis or ex vivo applications), who has an IL-1R-mediated disease or disorder, a symptom of an IL-1R-mediated disease or disorder, or the potential to develop an IL-1R-mediated disease or disorder, with the purpose to cure, heal, alleviate, relieve, alter, remedy, ameliorate, improve or affect an IL-1R-mediated disease or disorder, the symptoms of an IL-1R-mediated disease or disorder or the potential to develop an IL-1R-mediated disease or disorder. Such treatments may be specifically tailored or modified, based on knowledge obtained from the field of pharmacogenomics.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to the unexpected discovery of small molecule compounds that are useful to treat or ameliorate an IL-1R-mediated disease or disorder in a mammal. In certain embodiments, the disease or disorder includes scleroderma. In other embodiments, the compounds of the invention inhibit or modulate IL-1R signaling. In other embodiments, the compounds of the invention block or modulate the synthesis of collagen in the mammal and thus block or modulate fibrosis in the mammal. In yet other embodiments, the compounds of the invention are useful in combination with other therapeutic agents, such as but not limited to anakinra and/or rilonacept. In yet other embodiments, the compounds of the invention are useful in treating or preventing infectious, inflammatory and/or autoimmune diseases or disorders.

As demonstrated therein, in certain embodiments, the compounds of the invention were designed using the novel in silico screening technology called the Hybrid Structure Based (HSB) method. As a working hypothesis, inhibition of IL-1R leads to downstream modulation of collagen synthesis and thus controls fibrosis. In certain embodiments, the compounds of the invention block the interaction of IL-1α with 1L-1R. In other embodiments, the compounds of the invention block the interaction of IL-1β with 1L-1R. In yet other embodiments, the compounds of the invention block the interaction of IL-1α and IL-1β with 1L-1R.

Figure 7:
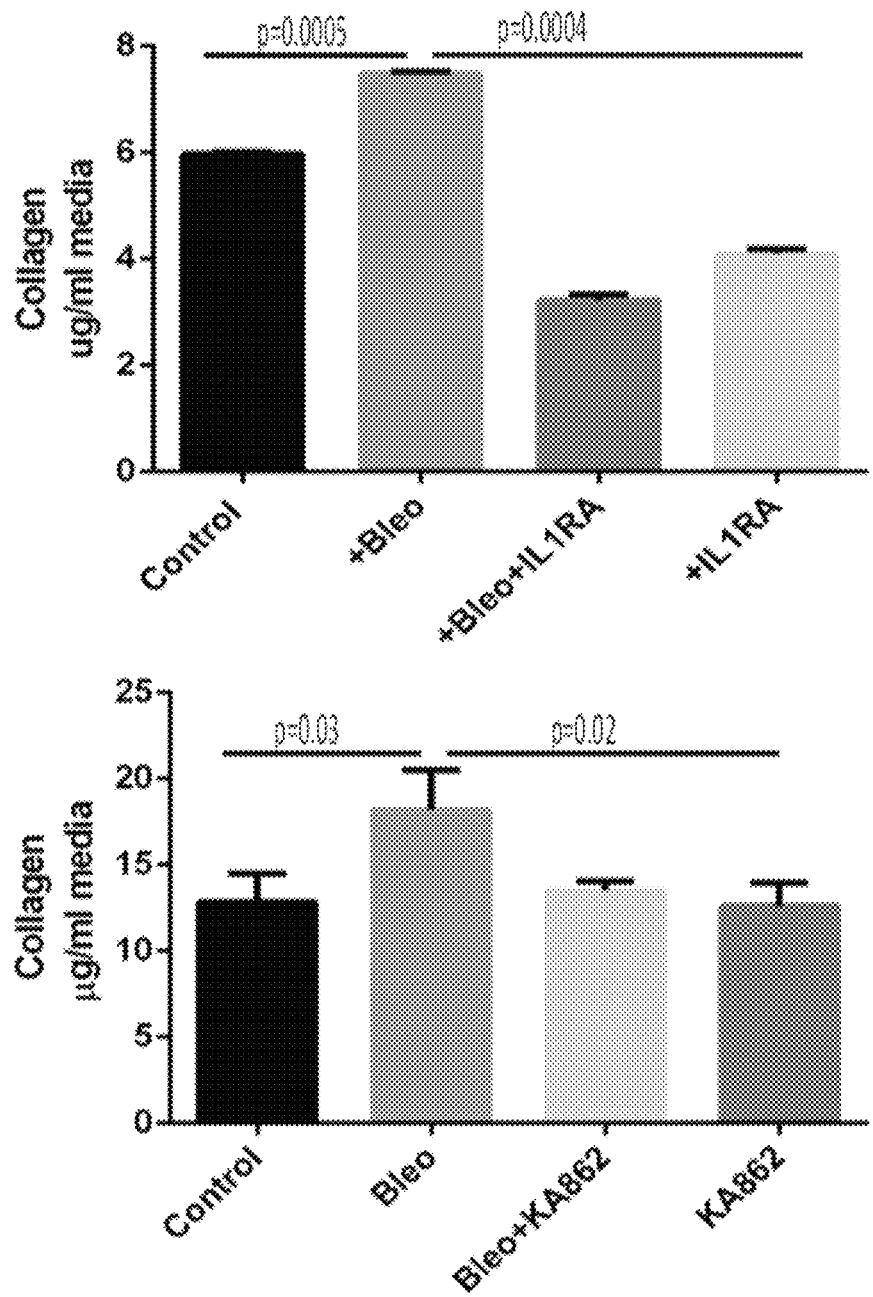
FIG. 7 is a set of bar graphs illustrating the finding that compounds of the invention are effective against bleomycin induced fibrosis in an in vitro model. Top graph: normal fibroblasts stimulated with bleomycin (Bleo)+IL-1RA (n=3); bottom graph: normal fibroblasts stimulated with Bleo+KA862 (n=3).
Figure 8:
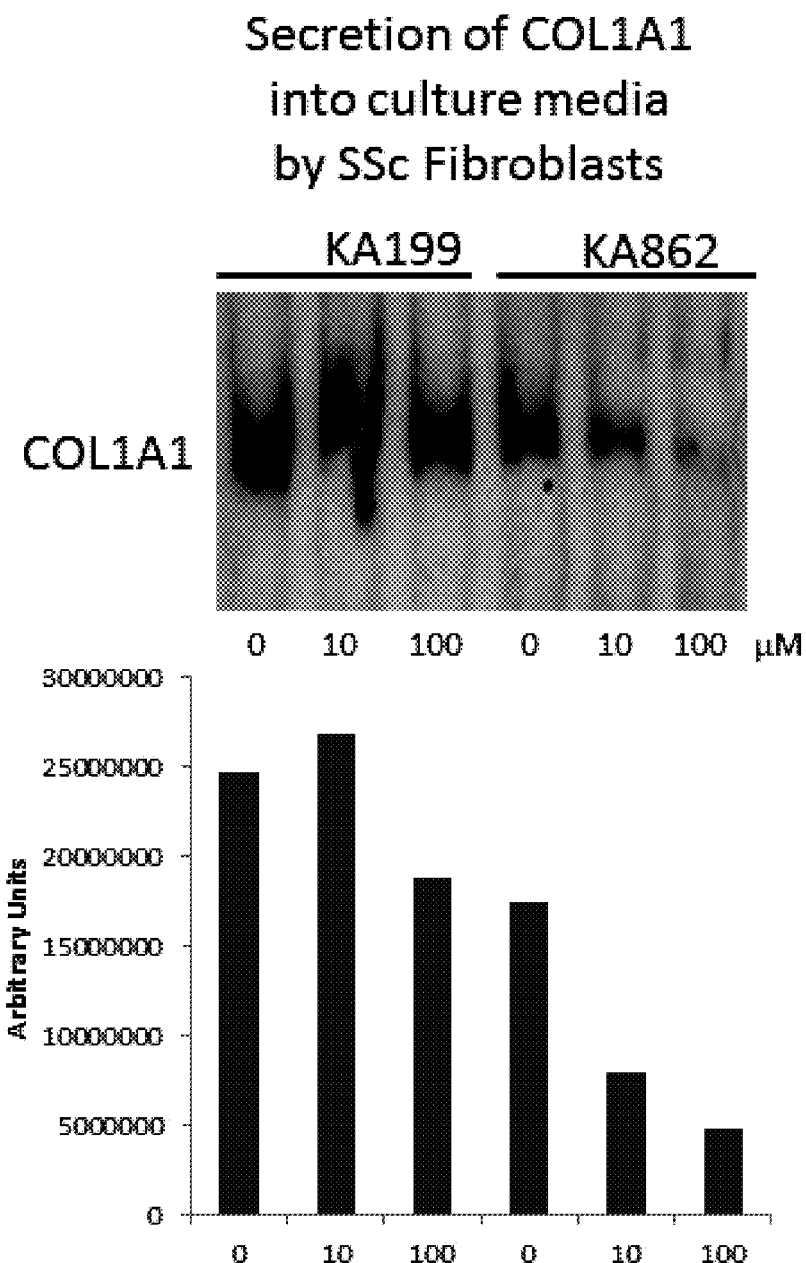
FIG. 8 is a set of images and bar graph illustrating the inhibition by compounds of the invention of secretion of COL1A1 into culture media by SSc fibroblasts.

As demonstrated herein, KA199, KA494, KA529, KA680, and KA862 were all effective at reducing total collagen secretion into the culture media as measured by hydroxyproline (FIG. 5). Western blotting for specific ECM proteins demonstrate that these compounds lower collagen secreted into culture media (FIGS. 7-8).

As demonstrated herein, KA494 and KA862 were found to be efficacious in blocking collagen synthesis when tested in vitro using fibroblasts derived from scleroderma patients and normal fibroblasts stimulated with 10 μM bleomycin to replicate scleroderma fibroblasts. Without wishing to be limited by any theory, designing a focused screening library allows for the identification of analogs with favorable drug-like properties and binding efficacy against IL-1R. Compounds of interest may be tested in vitro using patient-derived scleroderma fibroblasts, normal fibroblasts treated with bleomycin to increase collagen synthesis, and in vivo in scleroderma animal models.

Compounds and Compositions

The compounds useful in the methods of the invention may be synthesized using techniques well-known in the art of organic synthesis.

In one aspect, the compound is the compound of formula (I), or salt, tautomer or solvate thereof:

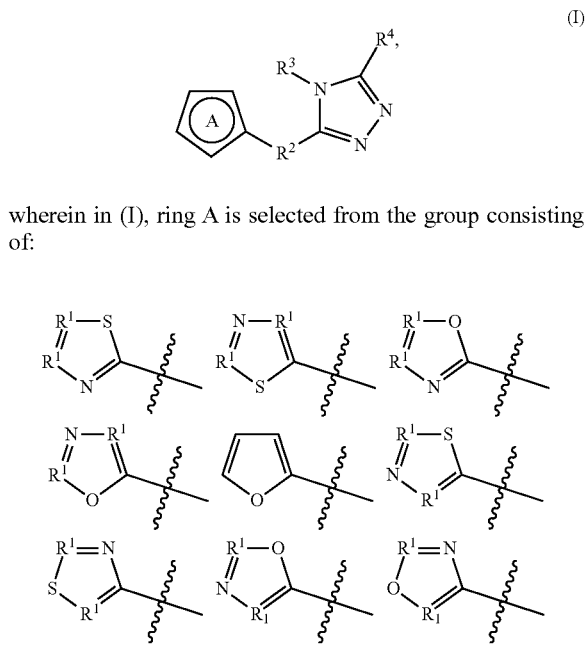

wherein in (I), ring A is selected from the group consisting of:

-continued

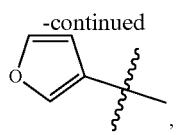

wherein in ring A one occurrence of R¹ is CR⁶ and the other occurrence of R¹ is N or CR⁷ and the furan rings are independently optionally substituted with R⁷; R² is selected from the group consisting of bond, —CH₂S—, —SCH₂—, —CH₂O—, —OCH₂—, —(CH₂)$_{1-6}$—, arylene, heteroarylene, and combinations thereof; R³ is selected from the group consisting of —C$_1$-C$_6$ alkyl, —C$_2$-C$_6$ alkenyl, —C$_1$-C$_6$ heteroalkyl, —(C$_0$-C$_3$ alkyl)-(C$_3$-C$_8$ cycloalkyl), —(C$_0$-C$_3$ alkyl)-(C$_4$-C$_{10}$ heterocyclyl), —(C$_0$-C$_3$ alkyl)-(C$_6$-C$_{10}$ aryl) and —(C$_0$-C$_3$ alkyl)-(C$_5$-C$_{10}$ heteroaryl), wherein the alkyl, alkenyl, heteroalkyl, cycloalkyl, heterocyclyl, aryl or heteroaryl group is independently optionally substituted; R⁴ is selected from the group consisting of —C$_1$-C$_6$ alkyl, —C$_1$-C$_6$ heteroalkyl, —(C$_0$-C$_3$ alkyl)-(C$_3$-C$_8$ cycloalkyl), —(C$_0$-C$_3$ alkyl)-(C$_4$-C$_{10}$ heterocyclyl), —(C$_0$-C$_3$ alkyl)-(C$_6$-C$_{10}$ aryl), —(C$_0$-C$_3$ alkyl)-(C$_5$-C$_{10}$ heteroaryl), —(CH₂)$_{1-3}$—C(=O)NH₂, —(CH₂)$_{1-3}$—C(=O)NHNHC(=O)R⁵, —S(CH₂)$_{1-3}$—C(=O)NH₂, —S(CH₂)$_{1-3}$—C(=O)NHR⁸, —S(CH₂)$_{1-3}$—C(=O)OR³ and —S(CH₂)$_{1-3}$—C(=O)NHNHC(=O)R⁵, wherein the alkyl, heteroalkyl, cycloalkyl, heterocyclyl, aryl or heteroaryl group is independently optionally substituted; each occurrence of R⁵ is independently —C$_4$-C$_{10}$ heterocyclyl, —C$_6$-C$_{10}$ aryl or —C$_5$-C$_{10}$ heteroaryl, wherein the heterocyclyl, aryl or heteroaryl group is independently optionally substituted; each occurrence of R⁶ is independently selected from the group consisting of —NHR⁸, —C(=O)OH, —C(=O)OR⁸ and —C(=O)NHR⁸; each occurrence of R⁷ is independently H, halo, —C$_1$-C$_6$ alkyl or —C$_3$-C$_{10}$ cycloalkyl, wherein the alkyl or cycloalkyl group is independently optionally substituted; and each occurrence of R⁸ is independently selected from the group consisting of —C$_1$-C$_6$ alkyl, —C$_1$-C$_6$ heteroalkyl, —(C$_0$-C$_3$ alkyl)-(C$_3$-C$_8$ cycloalkyl), —(C$_0$-C$_3$ alkyl)-(C$_4$-C$_{10}$ heterocyclyl), —(C$_0$-C$_3$ alkyl)-(C$_6$-C$_{10}$ aryl) and —(C$_0$-C$_3$ alkyl)-(C$_5$-C$_{10}$ heteroaryl), wherein the alkyl, heteroalkyl, cycloalkyl, heterocyclyl, aryl or heteroaryl group is independently optionally substituted.

In certain embodiments, ring A is selected from the group consisting of:

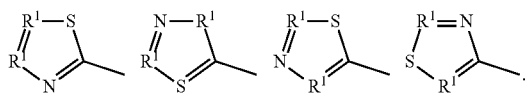

In other embodiments, ring A is selected from the group consisting of:

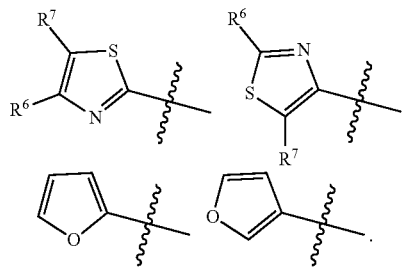

In certain embodiments, in ring A one occurrence of R¹ is CR⁶ and the other occurrence of R¹ is CR⁷.

In certain embodiments, R² is selected from the group consisting of —CH₂S—, —SCH₂— and —(CH₂)$_{1-6}$—.

In certain embodiments, R³ is selected from the group consisting of —C$_1$-C$_6$ alkyl, —C$_2$-C$_6$ alkenyl, —C$_3$-C$_8$ cycloalkyl, —(C$_0$-C$_3$ alkyl)-(C$_6$-C$_{10}$ aryl) and —(C$_0$-C$_3$ alkyl)-(C$_5$-C$_{10}$ heteroaryl), wherein the alkyl, alkenyl, cycloalkyl, aryl or heteroaryl group is independently optionally substituted. In other embodiments, R³ is selected from the group consisting of —C$_1$-C$_6$ alkyl, —C$_2$-C$_6$ alkenyl, furan-2-ylmethyl and furan-3-ylmethyl.

In certain embodiments, R⁴ is selected from the group consisting of C$_1$-C$_6$ alkyl, —(C$_0$-C$_3$ alkyl)-(C$_6$-C$_{10}$ aryl), —(C$_0$-C$_3$ alkyl)-(C$_5$-C$_{10}$ heteroaryl), —(CH₂)$_{1-3}$—C(=O)NH₂, —S(CH₂)$_{1-3}$—C(=O)NH₂, —S(CH₂)$_{1-3}$—C(=O)OR³ and —S(CH₂)$_{1-3}$—C(=O)NHNHC(=O)R⁵.

In certain embodiments, R⁵ is C$_6$-C$_{10}$ aryl or C$_5$-C$_{10}$ heteroaryl, wherein the aryl or heteroaryl group is independently optionally substituted.

In certain embodiments, R⁶ is selected from the group consisting of —NHR⁸ and —C(=O)NHR⁸.

In certain embodiments, R⁷ is H, halo or C$_1$-C$_6$ alkyl, wherein the alkyl group is optionally substituted. In other embodiments, R⁷ is H or halo.

In certain embodiments, R⁸ is selected from the group consisting of —(C$_0$-C$_3$ alkyl)-(C$_3$-C$_8$ cycloalkyl), —(C$_0$-C$_3$ alkyl)-(C$_6$-C$_{10}$ aryl) and —(C$_0$-C$_3$ alkyl)-(C$_5$-C$_{10}$ heteroaryl), wherein the alkyl, heteroalkyl, cycloalkyl, aryl or heteroaryl group is independently optionally substituted.

In certain embodiments, the compound of the invention is selected from the group consisting of:

cyclohexyl 2-((5-(((2-((3-chlorophenyl)amino)thiazol-4-yl)methyl)-4-(furan-2-yl methyl)-4H-1,2,4-triazol-3-yl)thio)acetate (KA862):

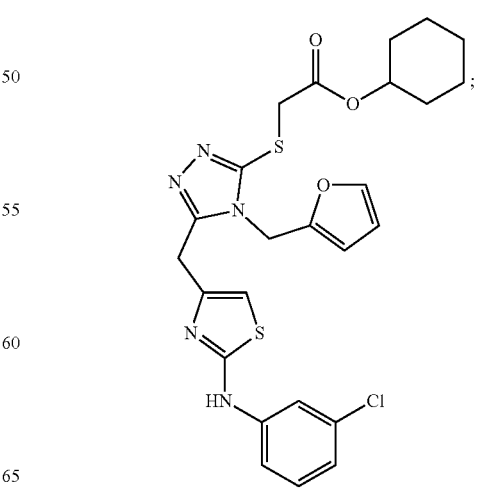

3-(4-(furan-2-ylmethyl)-5-(((2-(phenylamino)thiazol-4-yl)methyl)thio)-4H-1,2,4-triazol-3-yl)propanamide (1, FIG. 3):

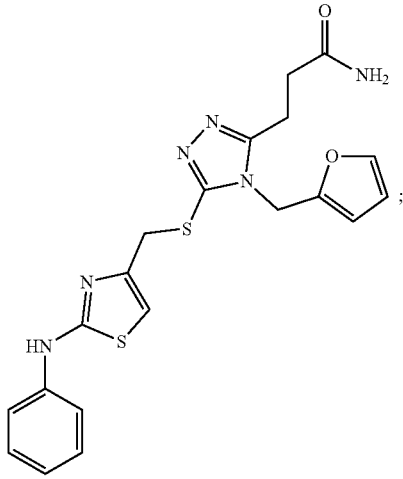 [SMILES: NC(=O)CCc1nnc(SCc2csc(Nc3ccccc3)n2)n1Cc1ccco1]

ethyl 2-(((4-(3-chlorophenyl)-5-(furan-2-yl)-4H-1,2,4-triazol-3-yl)thio)methyl) thiazole-4-carboxylate (2, FIG. 3):

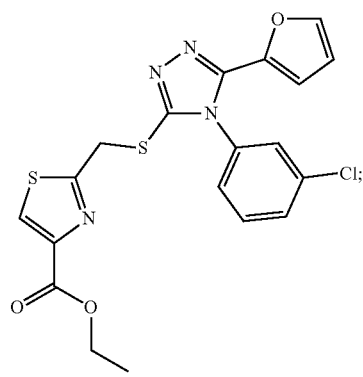 [SMILES: CCOC(=O)c1csc(CSc2nnc(-c3ccco3)n2-c2cccc(Cl)c2)n1]

2-(((4-(3-chlorophenyl)-5-methyl-4H-1,2,4-triazol-3-yl)thio)methyl)-N-(furan-2-yl methyl)thiazole-4-carboxamide (3, FIG. 3):

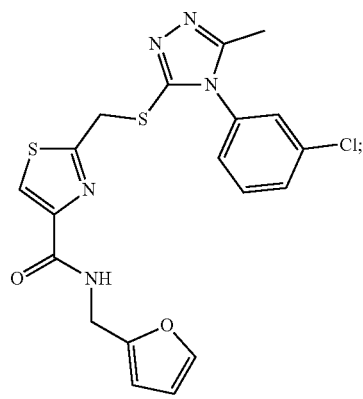 [SMILES: Cc1nnc(SCc2nc(C(=O)NCc3ccco3)cs2)n1-c1cccc(Cl)c1]

N'-(2-(4-butyl-5-((2-((3-chlorophenyl)amino)thiazol-4-yl)methyl)-4H-1,2,4-triazol-3-yl)thio)acetyl)furan-2-carbohydrazide (4, FIG. 3):

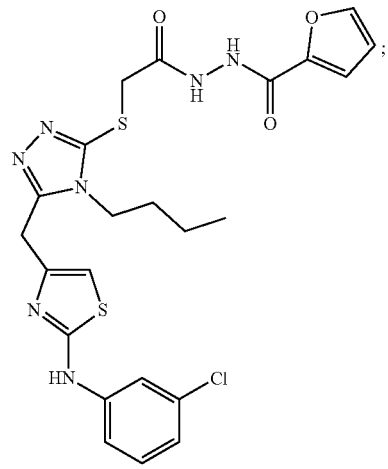 [SMILES: CCCCn1c(Cc2csc(Nc3cccc(Cl)c3)n2)nnc1SCC(=O)NNC(=O)c1ccco1]

2-((5-((2-(4-fluorophenyl)amino)thiazol-4-yl)methyl)-4-(furan-2-ylmethyl)-4H-1,2,4-triazol-3-yl)thio)acetamide (5, FIG. 3):

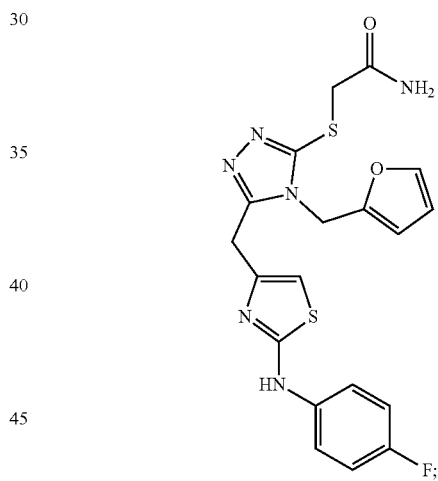

2-(((4-(3-chlorophenyl)-5-(furan-2-yl)-4H-1,2,4-triazol-3-yl)thio)methyl)-N-cyclohexylthiazole-4-carboxamide (6, FIG. 3):

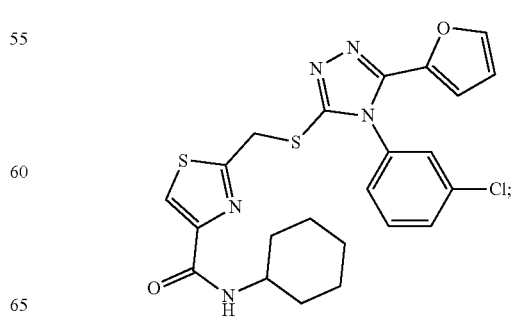

2-((4-allyl-5-(furan-2-yl)-4H-1,2,4-triazol-3-yl)thio)-N-(benzo[d]thiazol-2-yl) acetamide (KA426):

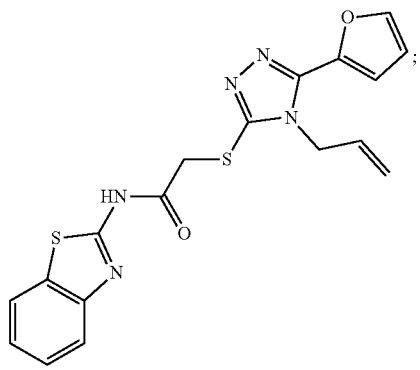 [SMILES: C=CCn1c(SCC(=O)Nc2nc3ccccc3s2)nnc1-c1ccco1]

N-(4,5-dimethylthiazol-2-yl)-2-((4-ethyl-5-(furan-2-yl)-4H-1,2,4-triazol-3-yl)thio)acetamide (KA420):

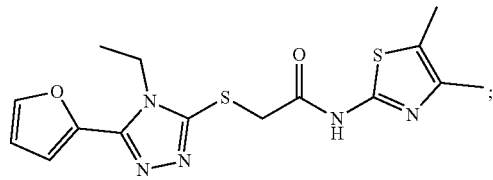 [SMILES: CCn1c(SCC(=O)Nc2nc(C)c(C)s2)nnc1-c1ccco1]

2-((5-((2-(4-ethoxyphenyl)amino)thiazol-4-yl)methyl)-4-ethyl-4H-1,2,4-triazol-3-yl)thio)-N-(furan-2-ylmethyl) acetamide (KA309):

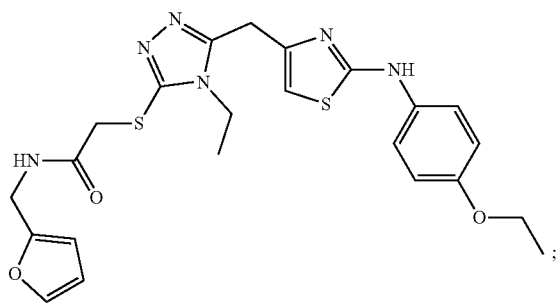 [SMILES: CCOc1ccc(Nc2nc(Cc3nnc(SCC(=O)NCc4ccco4)n3CC)cs2)cc1]

a salt, tautomer or solvate thereof, and any mixtures thereof.

In one aspect, the compound is the compound of formula (II), or salt, tautomer or solvate thereof:

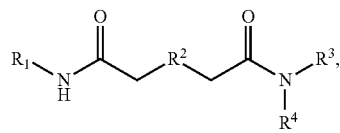

(II)

wherein in (II): $R^1$ and $R^3$ are independently selected from the group consisting of —($C_0$-$C_3$ alkyl)-($C_6$-$C_{10}$ aryl), and —($C_0$-$C_3$ alkyl)-($C_5$-$C_{10}$ heteroaryl), wherein the alkyl, aryl or heteroaryl group is independently optionally substituted; $R^2$ is S, S(=O) or S(=O)$_2$; $R^4$ is selected from the group consisting of —(CH$_2$)$_{1-3}$C(=O)OH, —(CH$_2$)$_{1-3}$C(=O)OR$^5$ and —(CH$_2$)$_{1-3}$C(=O)NHR$^5$; and each occurrence of $R^5$ is independently selected from the group consisting of —$C_1$-$C_6$ alkyl, —$C_1$-$C_6$ heteroalkyl, —($C_0$-$C_3$ alkyl)-($C_3$-$C_8$ cycloalkyl), —($C_0$-$C_3$ alkyl)-($C_4$-$C_{10}$ heterocyclyl), —($C_0$-$C_3$ alkyl)-($C_6$-$C_{10}$ aryl) and —($C_0$-$C_3$ alkyl)-($C_5$-$C_{10}$ heteroaryl), wherein the alkyl, heteroalkyl, cycloalkyl, heterocyclyl, aryl or heteroaryl group is independently optionally substituted.

In certain embodiments, $R^1$ is selected from the group consisting of —($C_6$-$C_{10}$ aryl), and —($C_5$-$C_{10}$ heteroaryl), wherein the aryl or heteroaryl groups is independently optionally substituted. In other embodiments, the aryl or heteroaryl group in $R^1$ is optionally substituted with at least one selected from the group consisting of halo, $C_1$-$C_6$ alkyl, hydroxy, and $C_1$-$C_6$ alkoxy. In yet other embodiments, $R^1$ is phenyl or benzo[d][1,3]dioxolyl.

In certain embodiments, $R^2$ is S(=O) or S(=O)$_2$. In other embodiments, $R^2$ is S(=O).

In certain embodiments, $R^3$ is selected from the group consisting of —($C_6$-$C_{10}$ aryl) and —($C_5$-$C_{10}$ heteroaryl), wherein the aryl or heteroaryl groups is independently optionally substituted. In other embodiments, $R^3$ is naphthyl, benzyl or phenyl, wherein the naphthyl, benzyl or phenyl group is optionally substituted. In yet other embodiments, the naphthyl, benzyl or phenyl group in $R^3$ is optionally substituted with at least one selected from the group consisting of halo, $C_1$-$C_6$ alkyl, hydroxy, and $C_1$-$C_6$ alkoxy.

In certain embodiments, $R^4$ is —(CH$_2$)$_{1-3}$C(=O)NHR$^5$. In other embodiments, $R^4$ is —(CH$_2$)C(=O)NHR$^5$.

In certain embodiments, $R^5$ is selected from the group consisting of —$C_1$-$C_6$ alkyl, —($C_0$-$C_3$ alkyl)-($C_3$-$C_8$ cycloalkyl), —($C_0$-$C_3$ alkyl)-($C_4$-$C_{10}$ heterocyclyl), —($C_0$-$C_3$ alkyl)-($C_6$-$C_{10}$ aryl), and —($C_0$-$C_3$ alkyl)-($C_5$-$C_{10}$ heteroaryl), wherein the alkyl, cycloalkyl, heterocyclyl, aryl or heteroaryl groups is independently optionally substituted. In other embodiments, $R^5$ is —$C_1$-$C_6$ alkyl or —($C_3$-$C_8$ cycloalkyl). In yet other embodiments, the alkyl or cycloalkyl group in $R^5$ is optionally substituted with at least one selected from the group consisting of halo, $C_1$-$C_6$ alkyl, hydroxy, and $C_1$-$C_6$ alkoxy.

In certain embodiments, the compound of formula (II) is:

N-(2-(cyclohexylamino)-2-oxoethyl)-2-((2-((4-fluorophenyl)amino)-2-oxoethyl) sulfinyl)-N-(naphthalen-1-yl)acetamide (KA494):

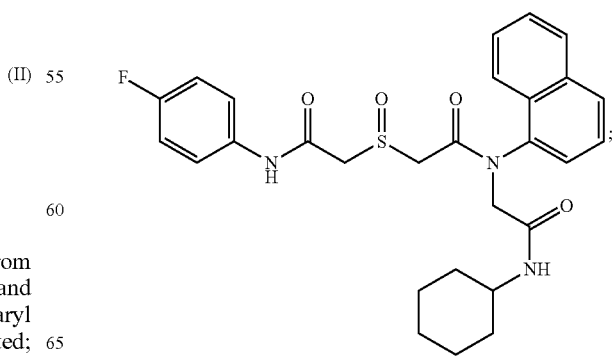

(N-cyclohexyl-N2-[({2-[(4-fluorophenyl)amino]-2-oxoethyl}sulfinyl)acetyl]-N²-1-naphthylglycinamide):

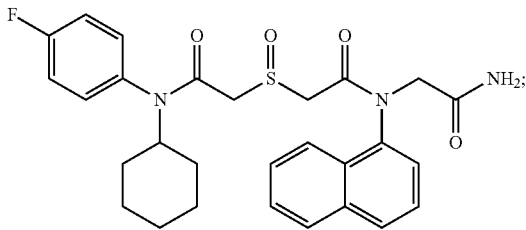 [SMILES: NC(=O)CN(C(=O)CS(=O)CC(=O)N(c1ccc(F)cc1)C1CCCCC1)c1cccc2ccccc12]

(N²-({[2-(1,3-benzodioxol-5-ylamino)-2-oxoethyl]sulfinyl}acetyl)-N²-(2-chlorobenzyl)-N-cyclopentylglycinamide) (KA680):

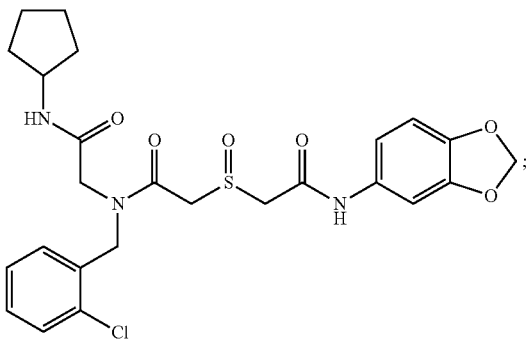 [SMILES: O=C(CS(=O)CC(=O)N(CC(=O)NC1CCCC1)Cc1ccccc1Cl)Nc1ccc2c(c1)OCO2]

N-(2-(tert-butylamino)-2-oxoethyl)-2-((2-((4-fluorophenyl)amino)-2-oxoethyl) sulfinyl)-N-(m-tolyl)acetamide (KA381):

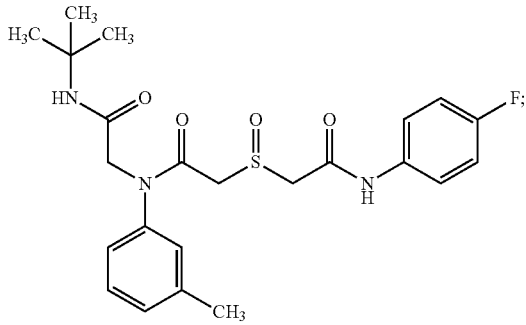 [SMILES: Cc1cccc(N(CC(=O)NC(C)(C)C)C(=O)CS(=O)CC(=O)Nc2ccc(F)cc2)c1]

or a salt, tautomer or solvate thereof.

In one aspect, the compound is the compound of formula (III), or salt, tautomer or solvate thereof:

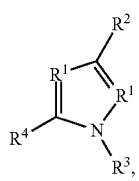

(III)

wherein in (III), each occurrence of $R^1$ is independently N or $CR^6$; $R^2$ is selected from the group consisting of —($C_0$-$C_3$ alkyl)-($C_4$-$C_{10}$ heterocyclyl), —($C_0$-$C_3$ alkyl)-($C_6$-$C_{10}$ aryl) and —($C_0$-$C_3$ alkyl)-($C_5$-$C_{10}$ heteroaryl), wherein the alkyl, heterocyclyl, aryl or heteroaryl group is independently optionally substituted; $R^3$ and $R^4$ are independently selected from the group consisting of —$(CH_2)_{1-3}$—$C(=O)OR^5$, —$(CH_2)_{1-3}$—$C(=O)NH_2$, —$(CH_2)_{1-3}$—$C(=O)NHR^5$, —$S(CH_2)_{1-3}$—$C(=O)NH_2$, —$S(CH_2)_{1-3}$—$C(=O)OR^5$ and —$S(CH_2)_{1-3}$—$C(=O)NHR^5$; each occurrence of $R^5$ is independently H, —$C_1$-$C_6$ alkyl, —$C_3$-$C_{10}$ cycloalkyl, —$C_6$-$C_{10}$ aryl, or heteroaryl, wherein the alkyl, cycloalkyl, aryl or heteroaryl group is independently optionally substituted; and each occurrence of $R^6$ is independently H, halo, —$C_1$-$C_6$ alkyl, —$C_3$-$C_{10}$ cycloalkyl, —$C_6$-$C_{10}$ aryl, or heteroaryl, wherein the alkyl, cycloalkyl, aryl or heteroaryl group is independently optionally substituted.

In certain embodiments, each occurrence of $R^1$ is N.

In certain embodiments, $R^2$ is selected from the group consisting of —$C_6$-$C_{10}$ aryl and —$C_5$-$C_{10}$ heteroaryl.

In certain embodiments, $R^3$ is selected from the group consisting of —$S(CH_2)_{1-3}$—$C(=O)NH_2$, —$S(CH_2)_{1-3}$—$C(=O)OR^5$ and —$S(CH_2)_{1-3}$—$C(=O)NHR^5$.

In certain embodiments, $R^4$ is selected from the group consisting of —$(CH_2)_{1-3}$—$C(=O)OR^5$, —$(CH_2)_{1-3}$—$C(=O)NH_2$, and —$(CH_2)_{1-3}$—$C(=O)NHR^5$.

In certain embodiments, the compound of the invention is (2-[5-{[2-(cyclopentylamino)-2-oxoethyl]sulfanyl}-3-(4-pyridinyl)-1H-1,2,4-triazol-1-yl]-N-(3-methoxy phenyl)acetamide) (KA529), or a salt, tautomer or solvate thereof:

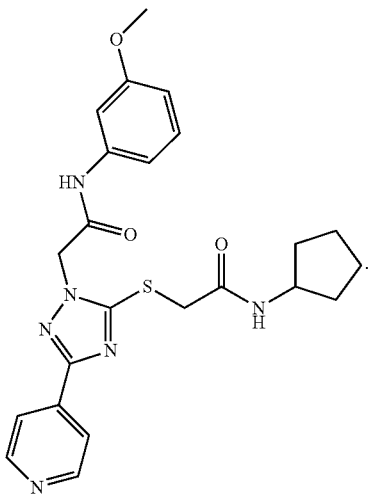 [SMILES: COc1cccc(NC(=O)Cn2nc(-c3ccncc3)nc2SCC(=O)NC2CCCC2)c1]

In one aspect, the compound is the compound of formula (IV), or salt, tautomer or solvate thereof:

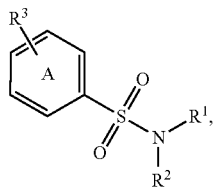

(IV)

wherein in (IV), $R^1$ is selected from the group consisting of —($C_0$-$C_3$ alkyl)-($C_4$-$C_{10}$ heterocyclyl), —($C_0$-$C_3$ alkyl)-($C_6$-$C_{10}$ aryl) and —($C_0$-$C_3$ alkyl)-($C_5$-$C_{10}$ heteroaryl), wherein the alkyl, heterocyclyl, aryl or heteroaryl group is independently optionally substituted; $R^2$ is selected from the group consisting of —$(CH_2)_{1-3}$—C(=O)$OR^4$, —$(CH_2)_{1-3}$—C(=O)$NH_2$, and —$(CH_2)_{1-3}$—C(=O)$NHR^4$; $R^3$ is —C(=O)$OR^4$, —C(=O)$NHR^4$ or —S(=O)$_2NHR^4$; each occurrence of $R^4$ is independently H, —$C_1$-$C_6$ alkyl, —$C_3$-$C_{10}$ cycloalkyl, —$C_6$-$C_{10}$ aryl, or heteroaryl, wherein the alkyl, cycloalkyl, aryl or heteroaryl group is independently optionally substituted; and A ring is optionally further substituted.

In certain embodiments, $R^1$ is selected from the group consisting of —$CH_2$—($C_4$-$C_{10}$ heterocyclyl), —$CH_2$—($C_6$-$C_{10}$ aryl) and —$CH_2$—($C_5$-$C_{10}$ heteroaryl). In certain embodiments, $R^2$ is —$(CH_2)_{1-3}$—C(=O)$NHR^4$. In certain embodiments, $R^3$ is —S(=O)$_2NHR^4$. In certain embodiments, $R^3$ is para or meta to the —S(=O)$_2NR^1R^2$ group. In certain embodiments, $R^3$ is para to the —S(=O)$_2NR'R^2$ group.

In certain embodiments, the compound of the invention is $N^2$-(1,3-benzodioxol-5-ylmethyl)-$N^2$-{[4-(cyclopentylsulfamoyl)phenyl]sulfonyl}-N-phenyl glycinamide (KA199), or a salt, tautomer or solvate thereof:

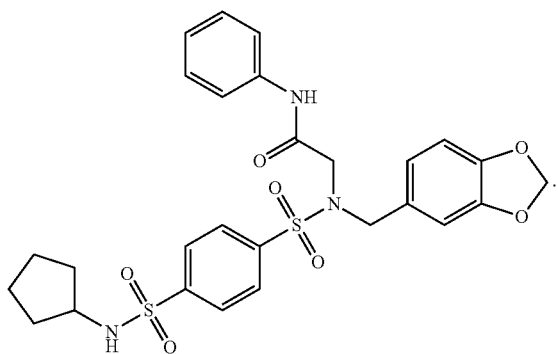 [SMILES: O=C(CN(Cc1ccc2c(c1)OCO2)S(=O)(=O)c1ccc(S(=O)(=O)NC2CCCC2)cc1)Nc1ccccc1]

In one aspect, the compound is the compound of formula (V), or salt, tautomer or solvate thereof:

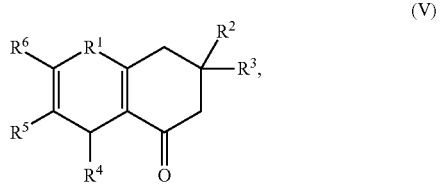

(V)

wherein in (V), $R^1$ is selected from the group consisting of O, NH and N($C_1$-$C_6$ alkyl), wherein the alkyl group is optionally substituted; $R^2$ is selected from the group consisting of H and —($C_1$-$C_6$ alkyl), wherein the alkyl group is optionally substituted; $R^3$ is selected from the group consisting of H, —($C_1$-$C_6$ alkyl) and aryl, wherein the alkyl or aryl group is optionally substituted; $R^4$ is optionally substituted aryl; $R^5$ is selected from the group consisting of —CN, —C(=O)OH and —C(=O)O($C_1$-$C_6$ alkyl), wherein the alkyl group is optionally substituted; and $R^6$ is methyl or $NH_2$.

In certain embodiments, in (V) $R^1$ is O or NH.
In certain embodiments, in (V) $R^2$ is H or methyl.
In certain embodiments, in (V) $R^3$ is H, methyl or phenyl, wherein the methyl or phenyl group is independently optionally substituted.

In certain embodiments, $R^4$ is optionally substituted naphthyl or anthracenyl.

In certain embodiments, $R^5$ is CN, —C(=O)$OCH_3$, —C(=O)OEt, or —C(=O)$OCH_2CH_2OCH_3$.

In certain embodiments, the compound of the invention is selected from the group consisting of:

2-amino-4-(2,7-diethoxynaphthalen-1-yl)-7,7-dimethyl-5-oxo-5,6,7,8-tetrahydro-4H-chromene-3-carbonitrile (KA092):

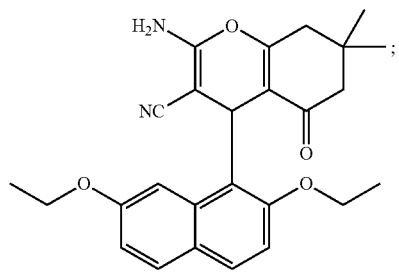 [SMILES: CCOc1ccc2ccc(OCC)c(C3C(C#N)=C(N)OC4=C3C(=O)CC(C)(C)C4)c2c1]

ethyl 2-methyl-4-(naphthalen-1-yl)-5-oxo-7-phenyl-1,4,5,6,7,8-hexahydroquinoline-3-carboxylate (KA031):

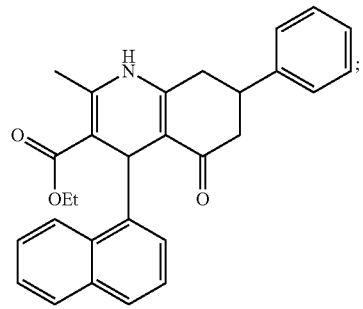 [SMILES: CCOC(=O)C1=C(C)NC2=C(C(=O)CC(c3ccccc3)C2)C1c1cccc2ccccc12]

methyl 7-(3,4-dimethoxyphenyl)-2-methyl-4-(naphthalen-1-yl)-5-oxo-1,4,5,6,7,8-hexahydroquinoline-3-carboxylate (KA306):

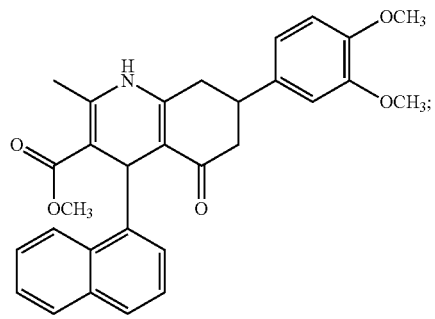 [SMILES: COC(=O)C1=C(C)NC2=C(C(=O)CC(c3ccc(OC)c(OC)c3)C2)C1c1cccc2ccccc12]

2-methoxyethyl 2-methyl-4-(naphthalen-1-yl)-5-oxo-1,4,5,6,7,8-hexahydroquinoline-3-carboxylate (KA695):

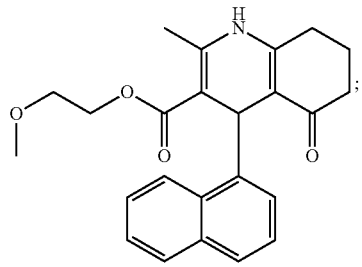 [SMILES: COCCOC(=O)C1=C(C)NC2=C(C(=O)CCC2)C1c1cccc2ccccc12]

methyl 7-(4-methoxyphenyl)-2-methyl-4-(naphthalen-1-yl)-5-oxo-1,4,5,6,7,8-hexahydroquinoline-3-carboxylate (KA819):

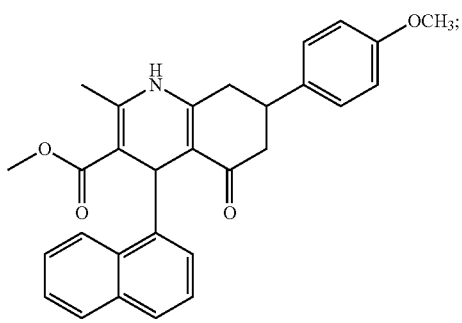 [SMILES: COC(=O)C1=C(C)NC2=C(C(=O)CC(c3ccc(OC)cc3)C2)C1c1cccc2ccccc12]

ethyl 4-(anthracen-9-yl)-2,7,7-trimethyl-5-oxo-1,4,5,6,7,8-hexahydroquinoline-3-carboxylate (KA820):

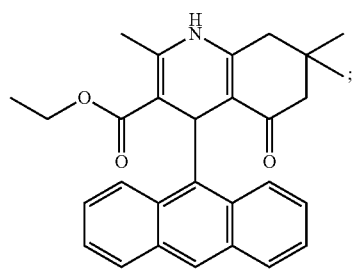 [SMILES: CCOC(=O)C1=C(C)NC2=C(C(=O)CC(C)(C)C2)C1c1c2ccccc2cc2ccccc12]

a salt, tautomer or solvate thereof, and any mixtures thereof.

In one aspect, the compound is the compound of formula (VI), 3-(furan-2-ylmethyl)-8-(naphthalen-1-yl)-6-oxo-3,4,7,8-tetrahydro-2H,6H-pyrido[2,1-b][1,3,5]thiadiazine-9-carbonitrile (KA321), or salt, tautomer or solvate thereof:

(VI)

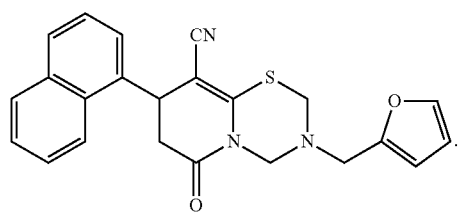

In one aspect, the compound is the compound of formula (VII), 6-amino-4-(2-hydroxynaphthalen-1-yl)-3-methyl-1-phenyl-1,4-dihydropyrano[2,3-c]pyrazole-5-carbonitrile (KA222), or salt, tautomer or solvate thereof:

(VII)

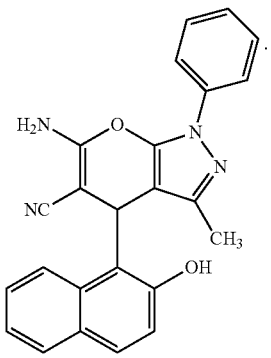

In one aspect, the compound is the compound of formula (VIII), 2-((3-cyano-4-(naphthalen-1-yl)-6-oxo-1,4,5,6-tetrahydropyridin-2-yl)thio)-N-phenylacetamide (KA095), or salt, tautomer or solvate thereof:

(VIII)

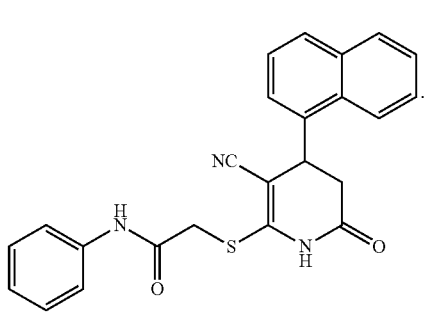

In one aspect, the compound is the compound of formula (IX), methyl 6-amino-5-cyano-2-(methoxymethyl)-4-(naphthalen-1-yl)-4H-pyran-3-carboxylate (KA097), or salt, tautomer or solvate thereof:

(IX)

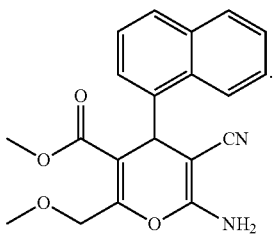

In one aspect, the compound is the compound of formula (X), 2-amino-4-(naphthalen-1-yl)-5-oxo-4H,5H-pyrano[3,2-c]chromene-3-carbonitrile (KA290), or salt, tautomer or solvate thereof:

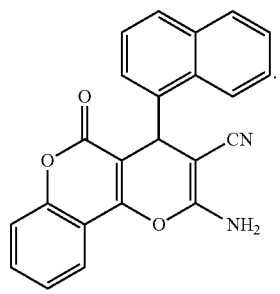

(X)

In one aspect, the compound is the compound of formula (XI), or salt, tautomer or solvate thereof:

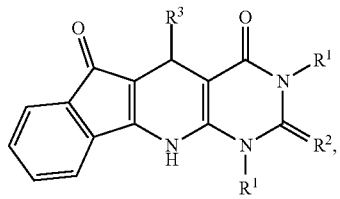

(XI)

wherein in (XI): each occurrence of $R^1$ is independently selected from the group consisting of H and methyl; $R^2$ is O or —NH; and $R^3$ is optionally substituted phenyl or naphthyl.

In certain embodiments, the compound of the invention is selected from the group consisting of:

1,3-dimethyl-5-(naphthalen-1-yl)-5,11-dihydro-1H-indeno[2',1':5,6]pyrido[2,3-d]pyrimidine-2,4,6(3H)-trione (KA811):

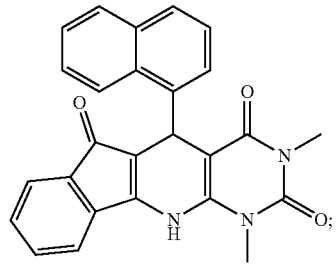 [SMILES: Cn1c2c(c(=O)n(C)c1=O)C(c1cccc3ccccc13)C1=C(N2)c2ccccc2C1=O]

2-amino-5-(naphthalen-1-yl)-5,11-dihydro-1H-indeno[2',1':5,6]pyrido[2,3-d]pyrimidine-4,6-dione (KA592):

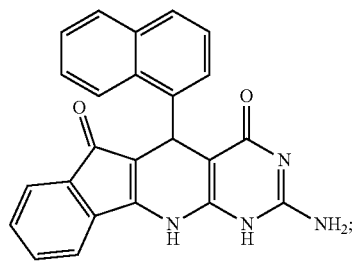 [SMILES: Nc1nc(=O)c2c([nH]1)NC1=C(C(=O)c3ccccc31)C2c1cccc2ccccc12]

a salt, tautomer or solvate thereof, and any mixtures thereof.

In one aspect, the compound is the compound of formula (XII), or salt, tautomer or solvate thereof:

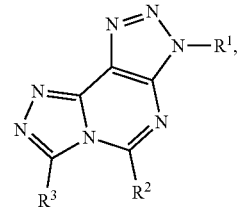

(XII)

wherein in (XII): $R^1$ is phenyl or benzyl, wherein the phenyl or benzyl group is optionally substituted; $R^2$ is H or methyl; and, $R^3$ is optionally substituted phenyl.

In certain embodiments, the compound of the invention is selected from the group consisting of:

3-(4-chlorophenyl)-7-(4-fluorophenyl)-3H-[1,2,3]triazolo[4,5-e][1,2,4]triazolo[4,3-c]pyrimidine (KA524):

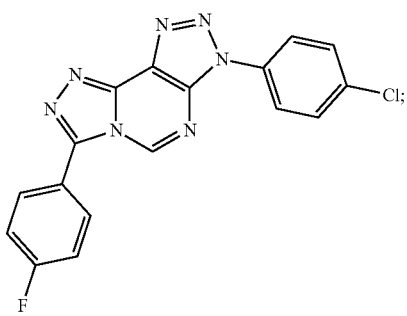 [SMILES: Fc1ccc(-c2nnc3c4nnn(-c5ccc(Cl)cc5)c4ncn23)cc1]

3-(2-chlorobenzyl)-7-(4-fluorophenyl)-5-methyl-3H-[1,2,3]triazolo[4,5-e][1,2,4]triazolo[4,3-c]pyrimidine (KA707):

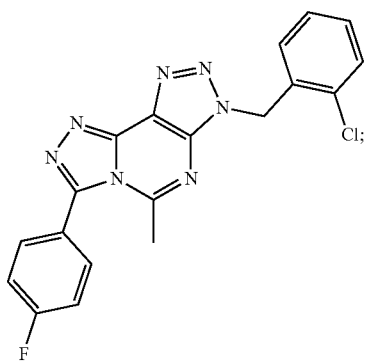 [SMILES: Cc1nc2c(nnn2Cc2ccccc2Cl)c2nnc(-c3ccc(F)cc3)n12]

7-(4-(1H-tetrazol-1-yl)phenyl)-3-(2-chlorobenzyl)-3H-[1,2,3]triazolo[4,5-e][1,2,4]triazolo[4,3-c]pyrimidine (KA521):

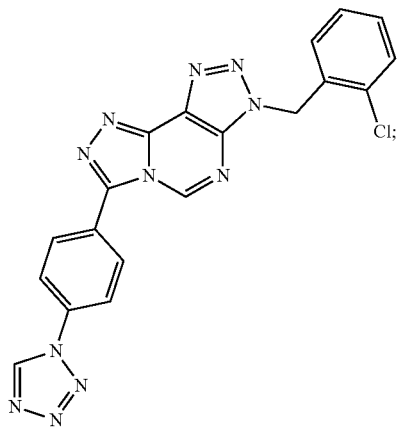 [SMILES: Clc1ccccc1Cn1nnc2c1ncn1c(-c3ccc(-n4cnnn4)cc3)nnc21]

a salt, tautomer or solvate thereof, and any mixtures thereof.

In one aspect, the compound is the compound of formula (XIII), or salt, tautomer or solvate thereof:

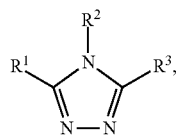

(XIII)

wherein in (XIII): $R^1$ is optionally substituted phenyl; $R^2$ is optionally substituted phenyl; and, $R^3$ is optionally substituted phenyl or heteroaryl.

In certain embodiments, in (XIII) $R^3$ is optionally substituted phenyl, optionally substituted pyridyl, optionally substituted quinolyl, or optionally substituted isoquinolyl.

In certain embodiments, the compound of the invention is selected from the group consisting of:

4-(5-(4-butoxyphenyl)-4-phenyl-4H-1,2,4-triazol-3-yl)-2-(p-tolyl)quinolone (KA154):

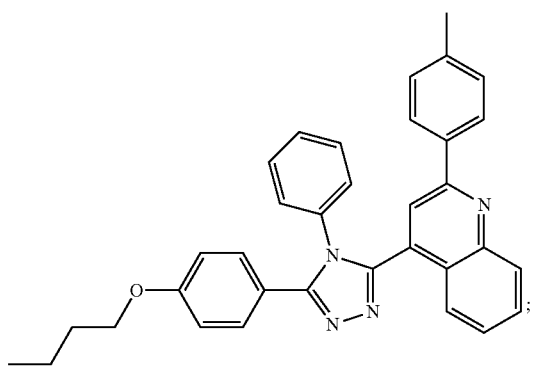 [SMILES: CCCCOc1ccc(-c2nnc(-c3cc(-c4ccc(C)cc4)nc4ccccc34)n2-c2ccccc2)cc1]

4-(5-(4-(tert-butyl)phenyl)-4-(p-tolyl)-4H-1,2,4-triazol-3-yl)pyridine (KA261):

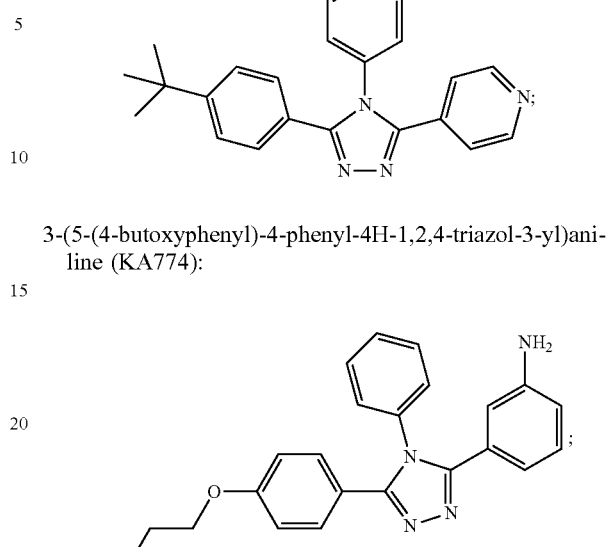

3-(5-(4-butoxyphenyl)-4-phenyl-4H-1,2,4-triazol-3-yl)aniline (KA774):

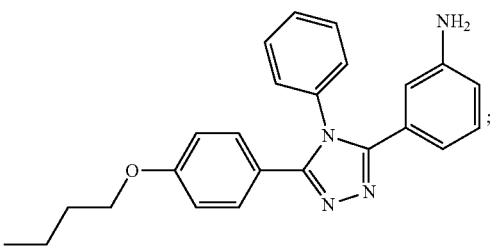 [SMILES: CCCCOc1ccc(-c2nnc(-c3cccc(N)c3)n2-c2ccccc2)cc1]

a salt, tautomer or solvate thereof, and any mixtures thereof.

The invention includes a pharmaceutical composition comprising at least one pharmaceutically acceptable carrier and at least one compound of the invention. In certain embodiments, the composition further comprises at least one additional therapeutic agent.

The compounds of the invention may possess one or more stereocenters, and each stereocenter may exist independently in either the (R) or (S) configuration. In one embodiment, compounds described herein are present in optically active or racemic forms. The compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form. In one embodiment, the compounds of the invention exist as tautomers. All tautomers are included within the scope of the compounds recited herein.

In one embodiment, compounds described herein are prepared as prodrugs. A "prodrug" is an agent converted into the parent drug in vivo. In one embodiment, upon in vivo administration, a prodrug is chemically converted to the biologically, pharmaceutically or therapeutically active form of the compound. In another embodiment, a prodrug is enzymatically metabolized by one or more steps or processes to the biologically, pharmaceutically or therapeutically active form of the compound.

In one embodiment, sites on, for example, the aromatic ring portion of compounds of the invention are susceptible to various metabolic reactions. Incorporation of appropriate substituents on the aromatic ring structures may reduce, minimize or eliminate this metabolic pathway. In one embodiment, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, the isotope comprises deuterium. In certain embodiments, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed. Isotopical labeling should not be constructed to be limited to the compounds of the invention, but rather applies to the compounds that may be used in combination with the compounds of the invention, such as but not limited to acetazolamide, almitrine, theophylline, caffeine, methylprogesterone and related compounds, sedatives that increase arousal threshold in sleep disordered breathing patients, benzodiazepine receptor agonists, orexin antagonists, tricyclic antidepressants, serotonergic modulators, adenosine and adenosine receptor and nucleoside transporter modulators, cannabinoids, orexins, melatonin agonists, ampakines, sodium oxybate, modafinil, armodafinil, and inhaled therapeutics. In certain embodiments, the oxybate salt is isotopically labeled with one or more deuteriums at the C-α position.

In one embodiment, the compounds described herein are labeled by other means, including, but not limited to, the use of chromophores or fluorescent moieties, bioluminescent labels, or chemiluminescent labels.

Methods

The invention includes a method of treating an IL-1R-mediated disease or disorder in a mammal in need thereof. The method comprises administering to the mammal a therapeutically effective amount of at least one compound of the invention, or a salt, tautomer or solvate thereof.

In certain embodiments, the compound of the invention is selected from the group consisting of: cyclohexyl 2-((5-((2-(3-chlorophenyl)amino)thiazol-4-yl)methyl)-4-(furan-2-yl methyl)-4H-1,2,4-triazol-3-yl)thio)acetate; 3-(4-(furan-2-ylmethyl)-5-(((2-(phenylamino)thiazol-4-yl)methyl)thio)-4H-1,2,4-triazol-3-yl)propanamide; ethyl 2-(((4-(3-chlorophenyl)-5-(furan-2-yl)-4H-1,2,4-triazol-3-yl)thio)methyl) thiazole-4-carboxylate; 2-(((4-(3-chlorophenyl)-5-methyl-4H-1,2,4-triazol-3-yl)thio)methyl)-N-(furan-2-yl methyl) thiazole-4-carboxamide; N'-2-((4-butyl-5-((2-((3-chlorophenyl)amino)thiazol-4-yl)methyl)-4H-1,2,4-triazol-3-yl) thio)acetyl)furan-2-carbohydrazide; 2-((5-((2-((4-fluorophenyl)amino)thiazol-4-yl)methyl)-4-(furan-2-ylmethyl)-4H-1,2,4-triazol-3-yl)thio)acetamide; 2-(((4-(3-chlorophenyl)-5-(furan-2-yl)-4H-1,2,4-triazol-3-yl)thio)methyl)-N-cyclohexylthiazole-4-carboxamide; 2-((4-allyl-5-(furan-2-yl)-4H-1,2,4-triazol-3-yl)thio)-N-(benzo[d]thiazol-2-yl) acetamide; N-(4,5-dimethylthiazol-2-yl)-2-((4-ethyl-5-(furan-2-yl)-4H-1,2,4-triazol-3-yl)thio)acetamide; 2-((5-((2-((4-ethoxyphenyl)amino)thiazol-4-yl)methyl)-4-ethyl-4H-1,2,4-triazol-3-yl)thio)-N-(furan-2-ylmethyl)acetamide; N-(2-(cyclohexylamino)-2-oxoethyl)-2-((2-(4-fluorophenyl)amino)-2-oxoethyl) sulfinyl)-N-(naphthalen-1-yl)acetamide; (N-cyclohexyl-N2-[({2-[(4-fluorophenyl)amino]-2-oxoethyl}sulfinyl)acetyl]-N²-1-naphthylglycinamide); (N²-({[2-(1,3-benzodioxol-5-ylamino)-2-oxoethyl]sulfinyl}acetyl)-N²-(2-chlorobenzyl)-N-cyclopentylglycinamide); N-(2-(tert-butylamino)-2-oxoethyl)-2-((2-(4-fluorophenyl)amino)-2-oxoethyl) sulfinyl)-N-(m-tolyl)acetamide; (2-[5-{[2-(μamino)-2-oxoethyl]sulfanyl}-3-(4-pyridinyl)-1H-1,2,4-triazol-1-yl]-N-(3-methoxy phenyl)acetamide); N²-(1,3-benzodioxol-5-ylmethyl)-N²-{[4-(cyclopentyl sulfamoyl) phenyl]sulfonyl}-N-phenylglycinamide; 2-amino-4-(2,7-diethoxynaphthalen-1-yl)-7,7-dimethyl-5-oxo-5,6,7,8-tetrahydro-4H-chromene-3-carbonitrile; ethyl 2-methyl-4-(naphthalen-1-yl)-5-oxo-7-phenyl-1,4,5,6,7,8-hexahydroquinoline-3-carboxylate; methyl 7-(3,4-dimethoxyphenyl)-2-methyl-4-(naphthalen-1-yl)-5-oxo-1,4,5,6,7,8-hexahydroquinoline-3-carboxylate; 2-methoxyethyl 2-methyl-4-(naphthalen-1-yl)-5-oxo-1,4,5,6,7,8-hexahydroquinoline-3-carboxylate; methyl 7-(4-methoxyphenyl)-2-methyl-4-(naphthalen-1-yl)-5-oxo-1,4,5,6,7,8-hexahydroquinoline-3-carboxylate; ethyl 4-(anthracen-9-yl)-2,7,7-trimethyl-5-oxo-1,4,5,6,7,8-hexahydroquinoline-3-carboxylate (KA820); 3-(furan-2-ylmethyl)-8-(naphthalen-1-yl)-6-oxo-3,4,7,8-tetrahydro-2H,6H-pyrido[2,1-b][1,3,5]thiadiazine-9-carbonitrile; 6-amino-4-(2-hydroxynaphthalen-1-yl)-3-methyl-1-phenyl-1,4-dihydropyrano[2,3-c]pyrazole-5-carbonitrile; 2-((3-cyano-4-(naphthalen-1-yl)-6-oxo-1,4,5,6-tetrahydropyridin-2-yl) thio)-N-phenylacetamide; methyl 6-amino-5-cyano-2-(methoxymethyl)-4-(naphthalen-1-yl)-4H-pyran-3-carboxylate; 2-amino-4-(naphthalen-1-yl)-5-oxo-4H,5H-pyrano[3,2-c]chromene-3-carbonitrile; 1,3-dimethyl-5-(naphthalen-1-yl)-5,11-dihydro-1H-indeno[2',1':5,6]pyrido[2,3-d]pyrimidine-2,4,6(3H)-trione; 2-amino-5-(naphthalen-1-yl)-5,11-dihydro-1H-indeno[2',1':5,6]pyrido[2,3-d]pyrimidine-4,6-dione; 3-(4-chlorophenyl)-7-(4-fluorophenyl)-3H-[1,2,3]triazolo[4,5-e][1,2,4]triazolo[4,3-c]pyrimidine; 3-(2-chlorobenzyl)-7-(4-fluorophenyl)-5-methyl-3H-[1,2,3]triazolo[4,5-e][1,2,4]triazolo[4,3-c]pyrimidine; 7-(4-(1H-tetrazol-1-yl)phenyl)-3-(2-chlorobenzyl)-3H-[1,2,3]triazolo[4,5-e][1,2,4]triazolo[4,3-c]pyrimidine; 4-(5-(4-butoxyphenyl)-4-phenyl-4H-1,2,4-triazol-3-yl)-2-(p-tolyl)quinolone; 4-(5-(4-(tert-butyl)phenyl)-4-(p-tolyl)-4H-1,2,4-triazol-3-yl)

pyridine; 3-(5-(4-butoxyphenyl)-4-phenyl-4H-1,2,4-triazol-3-yl)aniline; a salt, tautomer or solvate thereof; and any mixtures thereof.

In certain embodiments, the compound is administered to the mammal as part of a pharmaceutical composition. In other embodiments, the mammal is further administered at least one additional therapeutic agent. In yet other embodiments, the compound and the at least one additional therapeutic agent are co-administered to the mammal. In yet other embodiments, the compound and the at least one additional therapeutic agent are co-formulated. In yet other embodiments, the compound is administered to the mammal a given period of time before or after the at least one additional therapeutic agent is administered to the mammal. In yet other embodiments, the mammal is human.

Combination Therapies

In one non-limiting embodiment, the compounds of the present invention are useful in the methods of present invention in combination with one or more additional compounds useful for treating a disease or disorder contemplated within the invention, such as but not limited to an IL-1R-mediated disease or disorder, such as but not limited to scleroderma, or a complication or symptom thereof. These additional compounds may comprise compounds of the present invention or other compounds, e.g., commercially available compounds, known to treat, prevent, or reduce the symptoms of a disease or disorder contemplated within the invention.

In non-limiting examples, the additional compounds comprises anakinra, rilonacept, azathioprine, methotrexate, bosentan, etanercept, halofuginone, iloprost, cyclophosphamide, cyclosporin A, mycophenolate mofetil, intravenous immunoglobulin, pirfenidone, prednisone, rituximab, betaglycan peptides, basiliximab, sirolimus, alefacept, terguride, pomalidomide, and a tyrosine kinase inhibitor, such as imatinib, nilotinib or dasatinib.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the patient either prior to or after the onset of an IL-1R-mediated disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat an IL-1R-mediated disease or disorder in the patient. An effective amount of the therapeutic compound necessary to achieve a therapeutic effect may vary according to factors such as the state of the disease or disorder in the patient; the age, sex, and weight of the patient; and the ability of the therapeutic compound to treat an IL-1R-mediated disease or disorder in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of an IL-1R-mediated disease or disorder in a patient.

In one embodiment, the compositions of the invention are formulated using one or more pharmaceutically acceptable excipients or carriers. In certain embodiments, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It will be readily apparent to one skilled in the art that the frequency of administration of the various combination compositions of the invention will vary from individual to individual depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating an IL-1R-mediated disease or disorder, or a complication or symptom thereof) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of an IL-1R-mediated disease or disorder in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include nasal, inhalational, topical, oral, buccal, rectal, pleural, peritoneal, vaginal, intramuscular, subcutaneous, transdermal, epidural, intratracheal, otic, intraocular, intrathecal and intravenous.

The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of an IL-1R-mediated disease or disorder. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In a preferred embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention will depend on the age, sex and weight of the patient, the current medical condition of the patient and the progression of an IL-1R-mediated disease or disorder in the patient being treated. The skilled artisan will be able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1: Screening Studies

A hybrid structure based screening method was used to design small molecule inhibitors of IL-1R that bind at the antagonist site. Using the 21 amino acid peptide complexed IL-1R crystal structure as a template, a four point hybrid pharmacophore was designed and screened against a library of 3 million small molecules. The resulting 662 hits were filtered for drug-like properties, and 230 hits that cleared the filtering schemes were docked to the well-prepared IL-1R protein antagonist binding site using the molecular docking program GOLD (version 4.1).

The docked protein-ligand complexes were ranked using customized scoring schemes and five high ranking compounds (KA199, KA494, KA529, KA680, and KA862) were selected for in vitro validation. Molecular docking studies revealed that the compounds bind to the same site as the antagonist peptide or endogenous protein and hence can block the interaction of IL-1 with the IL-1R (FIG. 1).

Example 2: Collagen Synthesis

SSc fibroblasts were cultured with selected molecules of the invention, and total collagen synthesis was assessed with hydroxyproline. Four compounds demonstrated efficacy at 10 mM (FIG. 5). KA862 and KA494 were selected for further in vitro evaluation.

Example 3: Blockage of IL-1 Signaling

Figure 6:
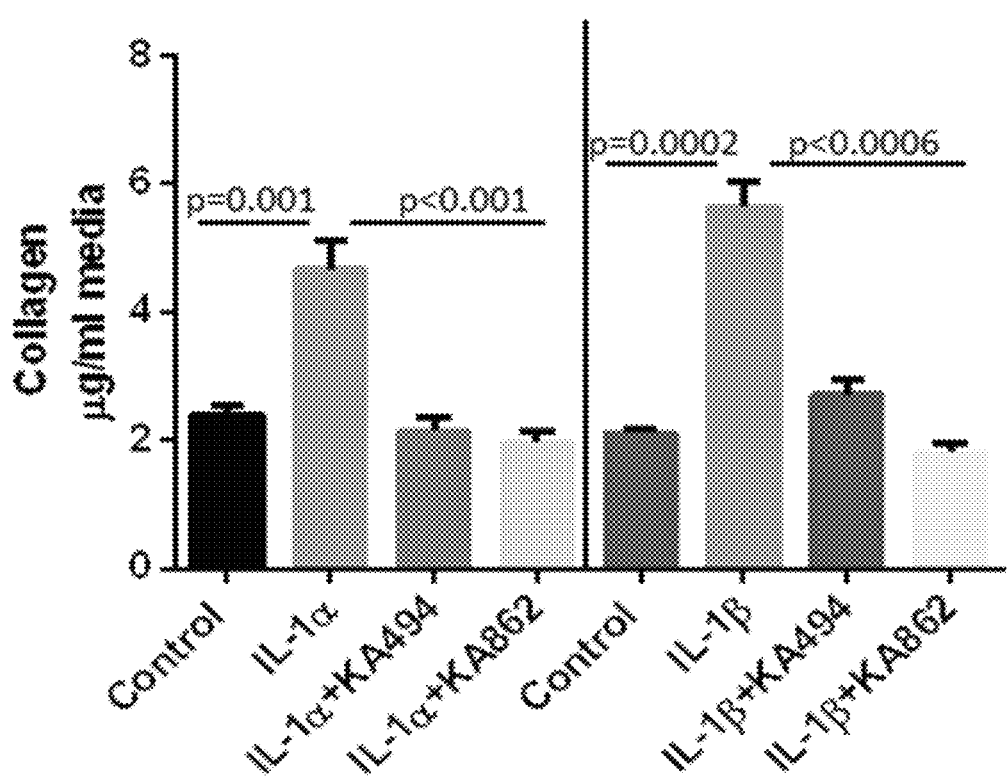
FIG. 6 is a graph illustrating target validation studies that assessed the direct blocking of IL-1 signaling in fibroblasts in normal fibroblasts.

FIG. 6 illustrates the finding that compounds of the invention directly blocks IL-1 signaling in normal fibroblasts.

Example 4: Bleomycin Induced Fibrosis

FIG. 7 illustrates the finding that compounds of the invention are effective against bleomycin induced fibrosis. Normal fibroblasts were treated with bleomycin and either IL-1RA or a compound of the invention, so as to inhibit collagen.

Example 5: Bleomycin Mouse Model of Fibrosis

The bleomycin mouse model of fibrosis is a well-established model for the study of initiating events of fibrosis in scleroderma. Substantively, fibrosis is induced with bleomycin in C57BL/6J mice. Skin fibrosis is induced by intradermal injections of bleomycin. Compounds of the invention, or vehicle, are administered daily by injecting the compounds or an equivalent volume of saline intraperitoneally. At the end of the study, mice are humanely euthanized, and lung, spleen, and dorsal skin, including tissue surrounding the bleomycin injection site, are harvested from each animal. Skin and lung are analyzed for fibrosis by histology, and spleen for inflammatory cells by flow cytometry. Oral administration of the compounds of the invention in this model is also evaluated.

Example 6

Figure 9:
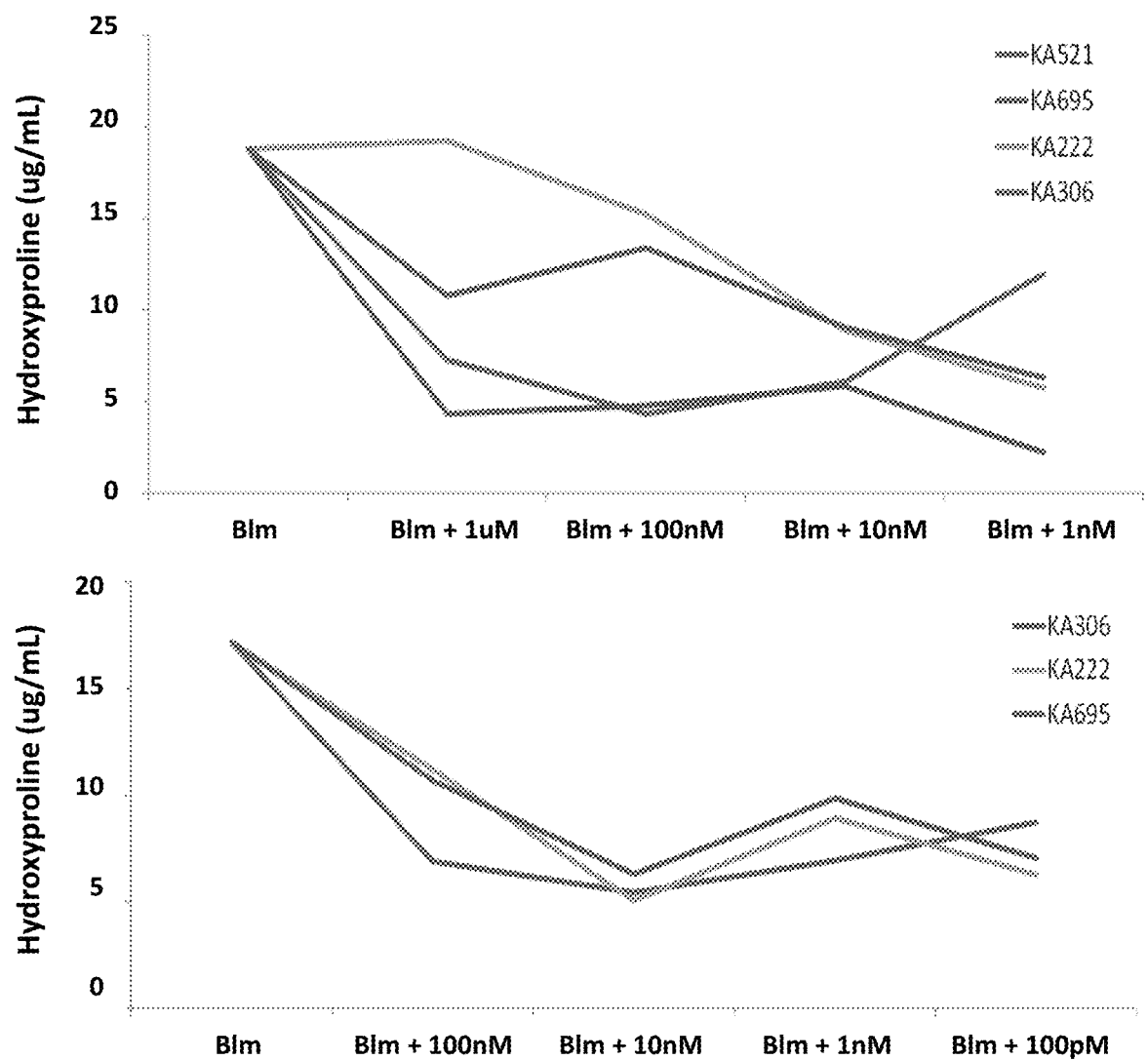
FIG. 9 is a set of graphs illustrating the $IC_{50}$ determination for KA521, KA222, KA306, and KA695. Decreasing concentrations of compound were tested against 10 µM bleomycin for 48 h and hydroxyproline measured in the culture media. $IC_{50}$ was found to be approximately 1 nM for KA222, KA306 and KA695 in this assay.

Compounds of the invention were analyzed to determine whether they were effective at preventing bleomycin induced fibrosis. Four compounds (KA521, KA222, KA306 and KA695) were selected for further testing and development. The experimental $IC_{50}$ for KA222, KA306 and KA695 was determined to be around 1 nM (FIG. 9).

Example 7

Figure 10:
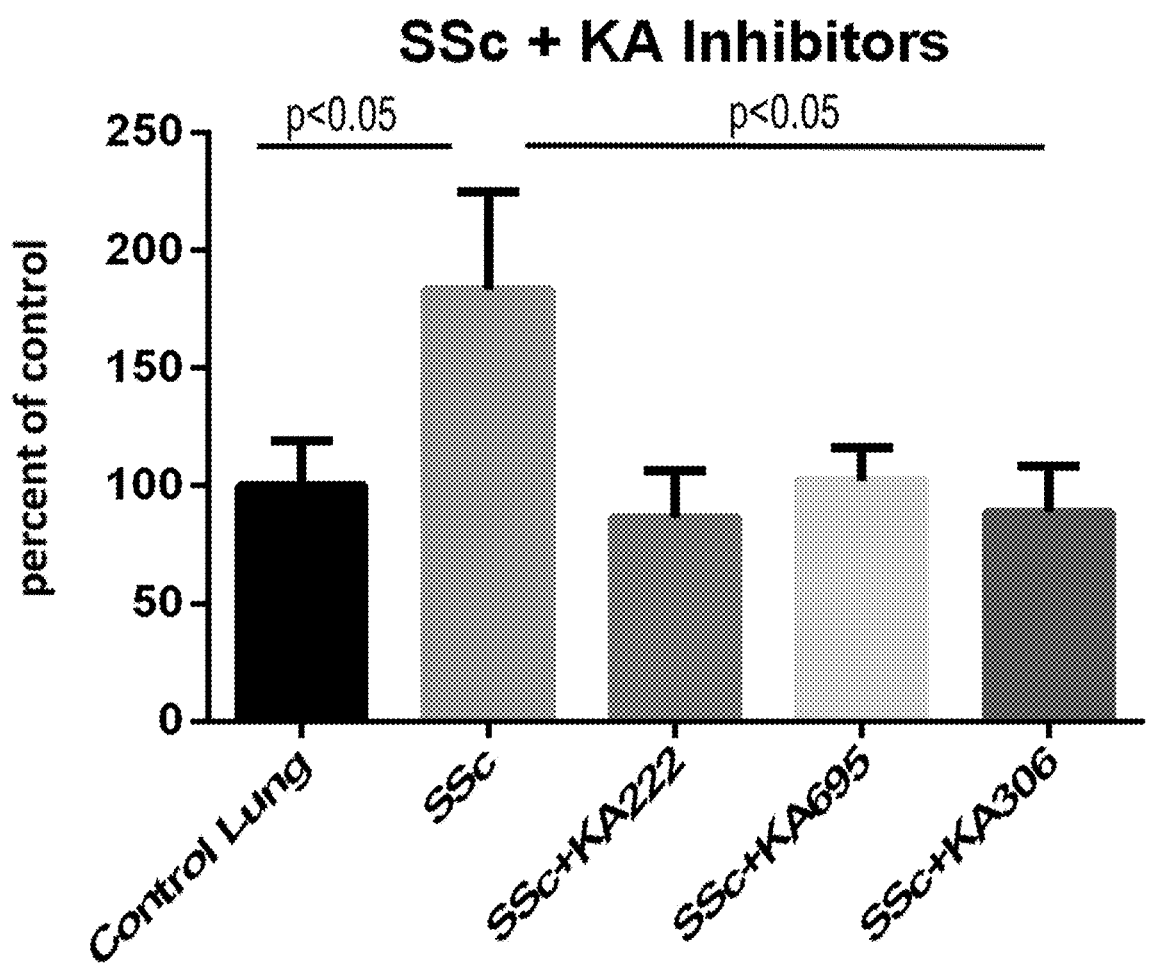
FIG. 10 is a graph illustrating the finding that exemplary compounds of the invention inhibit collagen production by SSc fibroblasts. SSc fibroblasts were treated for 48 h with 1 nM compound, and then culture media was recovered and hydroxyproline was measured. Samples were tested in triplicate across different patient samples and expressed as the mean±SEM (n=3 independent patient samples).

Three exemplary compounds of the invention were found to abrogate collagen synthesis by SSc fibroblasts at 1 nM (FIG. 10). The tested compounds significantly ameliorated collagen levels and returned collagen synthesis to nearly normal levels.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of relieving or improving at least one symptom of an IL-1R-mediated disease or disorder in a mammal in need thereof, the method comprising administering to the mammal a therapeutically effective amount of a compound having the structure:

6-amino-4-(2-hydroxynaphthalen-1-yl)-3-methyl-1-phenyl-1,4-dihydropyrano[2,3-c]pyrazole-5-carbonitrile:

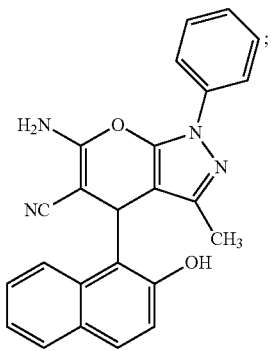 [SMILES: Cc1nn(-c2ccccc2)c2c1C(c1c(O)ccc3ccccc13)C(C#N)=C(N)O2]

or a salt, tautomer, or solvate thereof.

2. The method of claim 1, wherein the disease or disorder is selected from the group consisting of infectious, inflammatory, and autoimmune.

3. The method of claim 1, wherein the disease or disorder is selected from the group consisting of scleroderma, inflammation in general, systemic lupus erythematosus (lupus), Sjogren's syndrome, arthritis, myositis, Behcet's disease, inflammatory bowel disease, colitis, septic shock, chronic myelogenous leukemia, acute myelogenous leukemia, multiple myeloma, non-blood cancers, psoriasis, type I and type II diabetes, asbestosis, idiopathic pulmonary fibrosis, graft-versus-host disease, familial Mediterranean fever, stroke, epilepsy, and cryopyrin-associated periodic syndromes (CAPS).

4. The method of claim 3, wherein the disease or disorder is a non-blood cancer, and wherein the non-blood cancer is at least one selected from the group consisting of glioma, metastatic breast cancer, interleukin-1-producing cancer, pancreatic ductal adenocarcinoma, colorectal, melanoma, gastric carcinoma, cervical cancer, lung carcinoma, and ovarian carcinoma.

5. The method of claim 1, wherein the mammal is further administered at least one additional therapeutic agent.

6. The method of claim 5, wherein the at least one additional therapeutic agent comprises at least one selected from the group consisting of anakinra, rilonacept, azathioprine, methotrexate, bosentan, etanercept, halofuginone, iloprost, cyclophosphamide, cyclosporin A, mycophenolate mofetil, intravenous immunoglobulin, pirfenidone, prednisone, rituximab, beta-glycan peptides, basiliximab, sirolimus, alefacept, terguride, pomalidomide, and a tyrosine kinase inhibitor.

7. The method of claim 5, wherein the compound and the at least one additional therapeutic agent are co-administered to the mammal.

8. The method of claim 5, wherein the compound is administered to the mammal in a given period of time before or after the at least one additional therapeutic agent is administered to the mammal.

9. The method of claim 1, wherein the compound is formulated in a pharmaceutical composition that comprises at least one pharmaceutically acceptable excipient or carrier.

10. The method of claim 1, wherein the mammal is human.

* * * * *